United States Patent [19] [11] 4,324,799
Koch et al. [45] Apr. 13, 1982

[54] FUNGICIDAL THIOGLYCOLIC ACID ANILIDES, PROCESSES FOR THEIR MANUFACTURE AND PESTICIDAL COMPOSITIONS CONTAINING THEM

[75] Inventors: Manfred Koch, Eppstein; Hilmar Mildenberger; Burkhard Sachse, both of Kelkheim, all of Fed. Rep. of Germany

[73] Assignee: Hoechst Aktiengesellschaft, Frankfurt am Main, Fed. Rep. of Germany

[21] Appl. No.: 171,346

[22] Filed: Jul. 23, 1980

[30] Foreign Application Priority Data

Jul. 25, 1979 [DE] Fed. Rep. of Germany ....... 2930145
Apr. 3, 1980 [DE] Fed. Rep. of Germany ....... 3013104

[51] Int. Cl.³ .................. A01N 37/14; C07C 149/40; C07C 154/00; C07C 155/08
[52] U.S. Cl. .................. 424/301; 260/455 R; 260/455 A; 260/453.1; 260/347.2; 560/9; 562/426; 424/300; 424/304; 424/298; 424/278
[58] Field of Search ........... 260/455 R, 455 A, 453.1, 260/347.2; 560/9; 562/426; 424/300, 301, 304, 298, 278

[56] References Cited
U.S. PATENT DOCUMENTS
4,151,299 4/1979 Hubele ................ 260/455 A Primary Examiner—John M. Ford
Assistant Examiner—Robert C. Whittenbaugh
Attorney, Agent, or Firm—Curtis, Morris & Safford

[57] ABSTRACT

The present invention relates to new thioglycolic acid anilides of the formula I

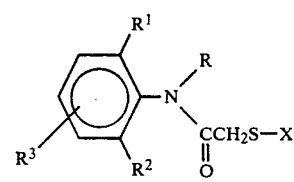

(I)

-continued

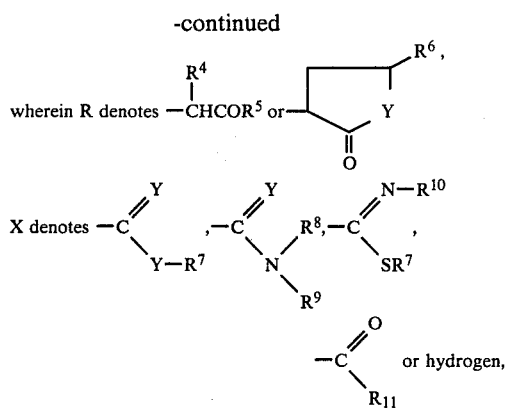

$R^1$ denotes $(C_1-C_4)$alkyl, halogen, $(C_1-C_3)$alkylthio, $(C_1-C_4)$alkoxy or $(C_3-C_4)$alkenyl,
$R^2$ denotes hydrogen, $(C_1-C_4)$ alkyl or halogen,
$R^3$, $R^4$ and $R^6$ denote hydrogen or methyl,
$R^5$ denotes hydroxy, $(C_1-C_4)$alkoxy, $(C_1-C_3)$alkylthio, $(C_1-C_2)$alkoxy -$(C_1-C_2)$alkoxy, amino, $(C_1-C_2)$alkylamino or di$(C_1-C_2)$alkylamino,
Y represents oxygen or sulfur,
$R^7$ represents optionally substituted $(C_1-C_6)$alkyl, $(C_3-C_6)$cycloalkyl, $(C_3-C_4)$alkenyl or $(C_3-C_4)$alkinyl,
$R^8$ represents hydrogen or $(C_1-C_4)$alkyl,
$R^9$ denotes optionally substituted $(C_1-C_4)$alkyl, $(C_3-C_4)$alkenyl, furfuryl, tetrahydrofurfuryl, with the proviso that if Y=S, the radicals $R^8$ and $R^9$ do not both denote $(C_1-C_4)$alkyl,
$R^{10}$ denotes -CN, optionally substituted $(C_1-C_4)$alkyl, allyl or furfuryl,
$R^{11}$ denotes hydrogen, optionally substituted $(C_1-C_4)$alkyl, $(C_2-C_4)$alkenyl, with the proviso that $R^{11}$ does not denote $(C_1-C_4)$ alkyl or halogen-substituted $(C_1-C_4)$alkyl, if R denotes

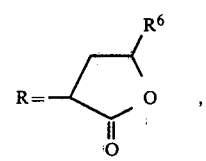

to processes for their manufacture and to their use as pesticidal compositions.

6 Claims, No Drawings

FUNGICIDAL THIOGLYCOLIC ACID ANILIDES, PROCESSES FOR THEIR MANUFACTURE AND PESTICIDAL COMPOSITIONS CONTAINING THEM

The invention relates to new thioglycolic acid anilides, processes for their preparation and their use as agents for combating pests, in particular in plant protection.

The compounds according to the invention have the general formula I

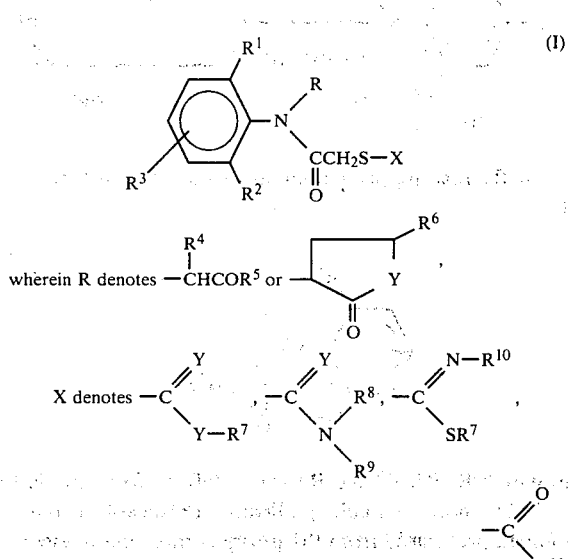

or hydrogen, $R^1$ denotes $(C_1-C_4)$-alkyl, halogen, $(C_1-C_3)$-alkylthio, $(C_1-C_4)$-alkoxy or $(C_3-C_4)$-alkenyl, $R^2$ denotes hydrogen, $(C_1-C_4)$-alkyl or halogen, $R^3$, $R^4$ and $R^6$ denote hydrogen or methyl, $R^5$ denotes hydroxyl, $(C_1-C_4)$-alkoxy, $(C_1-C_3)$-alkylthio, $(C_1-C_2)$-alkoxy-$(C_1-C_2)$-alkoxy, amino, $(C_1-C_2)$-alkylamino or di-$(C_1-C_2)$-alkylamino, Y denotes oxygen or sulfur, $R^7$ denotes $(C_1-C_6)$-alkyl, which can be substituted by $(C_1-C_2)$-alkoxy or halogen, or denotes $(C_3-C_6)$-cycloalkyl, $(C_3-C_4)$-alkenyl or $(C_3-C_4)$-alkynyl, $R^8$ denotes hydrogen or $(C_1-C_4)$-alkyl, $R^9$ denotes $(C_1-C_4)$-alkyl, which is optionally substituted by halogen or $(C_1-C_2)$-alkoxy, or denotes $(C_3-C_4)$-alkenyl, furfuryl or tetrahydrofurfuryl, with the proviso that if Y=S, the radicals $R^8$ and $R^9$ do not both denote $(C_1-C_4)$-alkyl, $R^{10}$ denotes —CN, $(C_1-C_4)$-alkyl, which is optionally substituted by halogen or $(C_1-C_2)$-alkoxy, or denotes allyl or furfuryl and $R^{11}$ denotes hydrogen, $(C_1-C_4)$-alkyl which is optionally substituted by one to three halogen atoms, $(C_1-C_2)$-alkoxy or $(C_1-C_2)$-alkylthio, or denotes $(C_2-C_4)$-alkenyl, with the proviso that in the case where R denotes

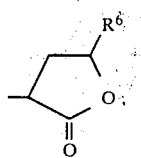

$R^{11}$ does not represent $(C_1-C_4)$-alkyl or halogen-substituted $(C_1-C_4)$-alkyl.

The radicals in formula I are preferably as follows: $R^1$ denotes methyl, ethyl, isopropyl, chlorine or bromine, $R^2$ denotes hydrogen or methyl, $R^3$, $R^4$ and $R^6$ denote hydrogen or methyl, $R^5$ denotes methoxy, ethoxy, propoxy, isopropoxy, methylthio or ethylthio, Y denotes oxygen or sulfur, $R^7$ denotes $(C_1-C_6)$-alkyl, which can be substituted by methoxy, ethoxy or chlorine, or denotes allyl, butenyl, propargyl or $(C_3-C_6)$-cycloalkyl, $R^8$ denotes hydrogen or $(C_1-C_4)$-alkyl, $R^9$ denotes $(C_1-C_4)$-alkyl, which is optionally substituted by $(C_1-C_2)$-alkoxy, or denotes $(C_3-C_4)$-alkenyl or furfuryl, with the proviso that if Y=S, the radicals $R^8$ and $R^9$ do not both denote $(C_1-C_4)$-alkyl, $R^{10}$ denotes —CN, $(C_1-C_4)$-alkyl, which is optionally substituted by $(C_1-C_2)$-alkoxy, or denotes allyl or furfuryl and $R^{11}$ denotes hydrogen, $(C_1-C_4)$-alkyl which is optionally substituted by one to three halogen atoms, $(C_1-C_2)$-alkoxy or $(C_1-C_2)$-alkylthio, or denotes $(C_2-C_4)$-alkenyl, with the proviso that in the case where R denotes

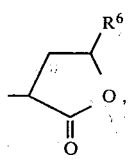

$R^{11}$ does not represents $(C_1-C_4)$-alkyl or halogen-substituted $(C_1-C_4)$-alkyl.

The use of fungicides from the dithiocarbamate series, such as, for example, mancozeb or maneb, or from the series of perchloromethylmercaptan derivatives, such as, for example, captafol, for combating rot diseases in plants caused by fungi of the genus Phytophthora is known. Phytophthora strains which attack the foliage and stalks above the ground can be combated with these active compounds, whilst soil-borne pathogens of the genus Phytophthora and Pythium which attack the roots of the plants are not affected. It is also known that acylated anilinoacetic acid derivatives and anilinopropionic acid derivatives such as are described in German Offenlegungsschriften Nos. 2,350,944, 2,643,445, 2,513,730, 2,513,789, 2,515,091 and 2,643,477 also have, in addition to a herbicidal activity, a fungicidal action against fungi of the Oomycetes family.

In contrast, esters of thiocarbonic acid or dithiocarbonic acid have hitherto been disclosed as active compounds which can be utilized in agriculture in only a small number of cases (for example as herbicides) (German Auslegeschrift No. 1,031,571 and French Pat. No. 1,171,404).

It has now been found, surprisingly, that the thioglycolic acid anilides of the formula I according to the invention have an outstanding fungicidal action, especially against Oomycetes belonging to the class of Phycomycetes, such as, for example, Pythium, Phytophthora, Peronospora, Pseudoperonospora and Plasmopara. In addition, they also have an action against fungi of the classes Ascomycetes, Basidiomycetes (for example rust fungi) and Fungi imperfecti. Using these compounds, fungi on the most diverse crop plants, such as, for example, maize, rice, cereals, sugar-beet, vegetables, plants of the cucumber family, potatoes, tomatoes, beet, hops, tobacco, varieties of citrus fruit and paprika, ornamental plants, cocoa, bananas and rubber, can be combated or inhibited, or their occurrence on these plants can be completely prevented. Some of the compounds of the formula I have a systemic action. They can also be used as dressing agents for combating seed-borne fungi on seeds or for combating the phytopathogenic fungi occurring in the soil.

The action of the compounds of the formula I according to the invention is therefore also to be described as extremely surprising because, inter alia, corresponding alkylthioacetanilides such as are described in the above-mentioned German Offenlegungsschrift No. 2,515,091 have only a very slight fungicidal action against Phytophthora, in particular against soil-borne species of Phytophthora and fungi of the Phythium family.

The invention thus also relates to fungicidal agents containing a compound of the formula I.

It is possible to prepare compounds of the formula I by various methods, and this preparation can be carried out, for example, by one of the processes listed below:

(a) By reacting a compound of the general formula II

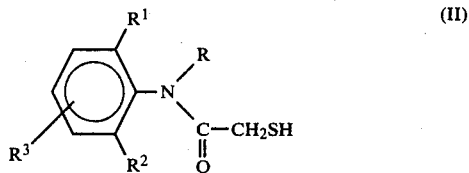

in which R, $R^1$, $R^2$ and $R^3$ are as defined for formula I, with, depending on the radical X in formula I, ($a_1$) acid halides of the general formula III

in which X is as defined for formula I and preferably denotes

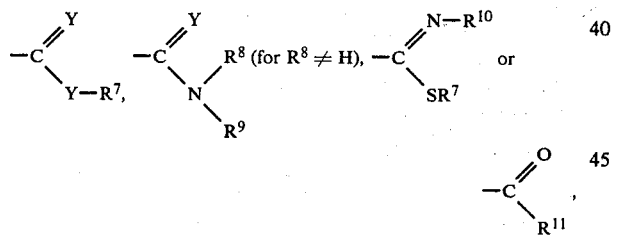

wherein the radicals Y, $R^7$, $R^8$, $R^9$, $R^{10}$ and $R^{11}$ are as defined for formula I and Hal represents halogen, preferably chlorine or bromine, it also being possible, if desired, to use the corresponding acid anhydride of the formula IIIa

wherein X is as defined for formula III, instead of the acid halide Hal-X of the formula III, or ($a_2$) for compounds of the formula I in which X denotes

and $R^8$ denotes H, with isocyanates of the formula IIIb

wherein Y and $R^9$ are as defined for formula I, according to the following equation:

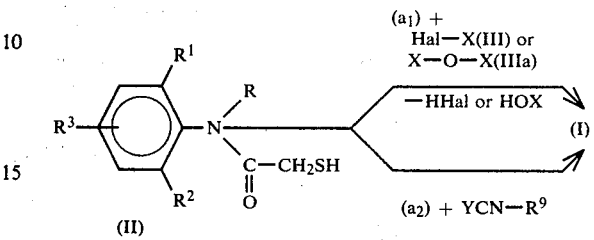

(b) By reacting a compound of the general formula IV

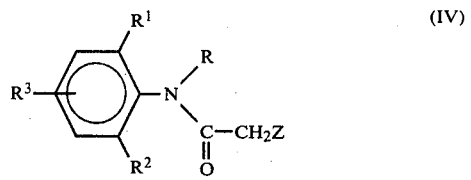

in which R, $R^1$, $R^2$ and $R^3$ are as defined for formula I and Z denotes a nucleophilically replaceable leaving radical, preferably from the group comprising halogen, tosylate and mesylate, in particular chlorine or bromine, with a compound of the general formula V

in which X is as defined for formula I and Me denotes an inorganic or organic cation, preferably sodium, potassium, ½-calcium, ½-magnesium or ammonium, according to the following equation:

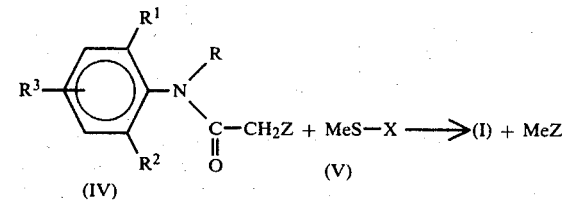

(c) By acylating aniline derivatives of the general formula VI

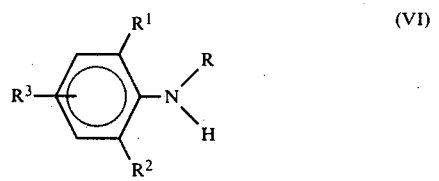

in which R, $R^1$, $R^2$ and $R^3$ are as defined for formula I, with acid halides or acid anhydrides of the general formula VII

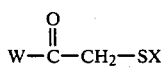

in which X is as defined for formula I and W denotes a halogen atom, preferably chlorine or bromine, or the radical

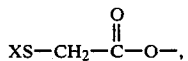

wherein X is as defined for formula VII, according to the following equation:

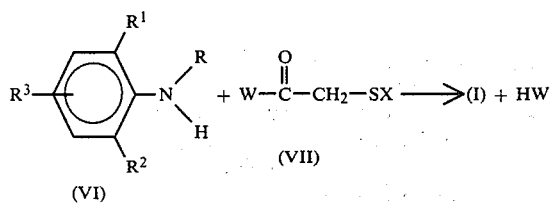

Compounds of the formula I in which X denotes

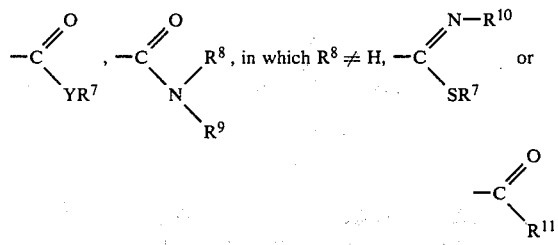

can preferably be prepared by this procedure.

(d) For compounds of the formula I in which X denotes

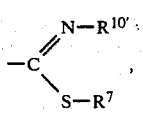

by alkylating compounds of the general formula VIII

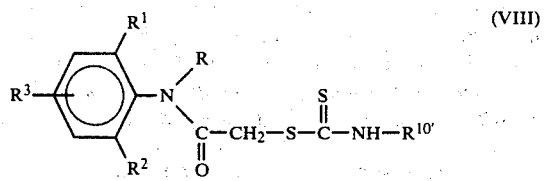

in which R, $R^1$, $R^2$ and $R^3$ are as defined for formula I and $R^{10'}$ represents $(C_1-C_4)$-alkyl, which is optionally substituted by $(C_1-C_2)$-alkoxy, or allyl or furfuryl, with halides or sulfates of the formula IX $$Q-R^7 \quad (IX)$$

in which $R^7$ is as defined for formula I and Q denotes halogen or

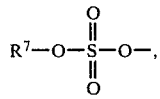

preferably chlorine, bromine or iodine, according to the following equation:

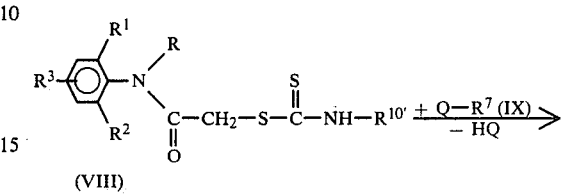

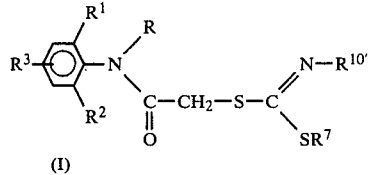

The reactions can be carried out in the presence or absence of solvents or diluents which are inert towards the reactants. Examples of possible solvents are: aliphatic, aromatic or araliphatic hydrocarbons, such as benzene, toluene, xylene or petroleum ether, halogenated hydrocarbons, such as chlorobenzene or methylene chloride, ethers, such as dialkyl ether, dioxan or tetrahydrofuran, nitriles, such as acetonitrile, dialkylated amides, such as dimethylformamide, ketones, such as acetone or methyl ethyl ketone, and, in the case of a preparation by either method (b) or (d), also alcohols, such as methanol, ethanol or ethylene glycol, or water, as well as mixtures of such solvents.

The reaction temperatures are not critical and are between $-20°$ and $+180°$ C., preferably between $0°$ and $120°$ C.

The reactions according to methods $(a_1)$, (c) and (d) can be carried out in the presence or absence of acid-binding agents and the reaction according to method $(a_2)$ can be catalyzed by adding bases, such as, for example, pyridine or triethylamine. Examples of possible acid-binding agents are: trialkylamines, such as triethylamine, pyridine or inorganic bases, such as, for example, metal oxides or metal hydroxides, for example calcium oxide or sodium hydroxide or carbonates, such as potassium carbonate.

If no acid-binding agents are added, the reactions according to methods $(a_1)$ or (c) are advantageously carried out at elevated temperature and, for example, the hydrogen halide formed is removed from the reaction mixture.

If the preparation of the compounds of the formula I is carried out in solvents in which one of the reactants has only a low solubility, for example using non-polar solvents such as hydrocarbons or water, acceleration of the reaction can be achieved by adding catalysts, such as, for example, crown ethers or quaternary ammonium or phosphonium salts.

Compounds of the formula II are prepared by methods which are in themselves known, such as are described, for example, in Houben-Weyl, Methoden der organischen Chemie (Methods of Organic Chemistry), Volume 9, 4th edition (1955) pages 12–18. A preferred method of preparation which is available is the reductive splitting of disulfides of the formula X, for example by means of zinc, according to the following equation:

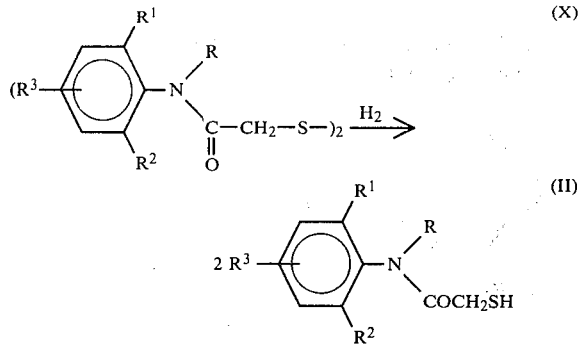

The aniline derivatives of the formula VI used as a starting material can be prepared, for example, in accordance with the method in: J. Org. Chem. 30, 4101 (1965); German Offenlegungsschrift No. 2,212,268; U.S. Pat. No. 4,012,519; and Tetrahedron 1967, 487 and 493.

The starting materials of the formula IV can be prepared from the aniline derivatives of the formula VI by acylation, for example by means of chloroacetyl chloride or bromoacetyl chloride.

The acid halides of the formula III, isocyanates of the formula IIIb and compounds of the formula V are known (compare Houben-Weyl, Methoden der organischen Chemie (Methods of Organic Chemistry), Volume 9, 4th edition (1955), pages 808–809, pages 813–16, page 820, page 829, page 835, page 838, pages 842–46 and page 849).

The acid halides of the formula VII can be prepared by methods with which the expert is familiar, for example starting from thioglycolic acid or chloroacetic acid.

The compounds of the formula I in which R denotes

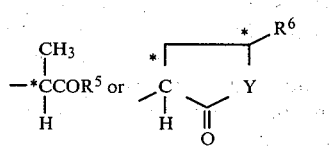

have asymmetric carbon atoms. They therefore in general exist as racemic mixtures of enantiomeric forms. The enantiomeric forms have a different biological activity. In the case where R denotes

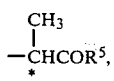

the compounds of the formula I with the D-(or R)-configuration have an increased activity compared with the racemate and those with the L-(or S)-configuration. A number of compounds of the formula I with the D-configuration are mentioned as examples. They are distinguished from the racemic compounds by the addition of the letters "AD". Controlled synthesis of the pure D-isomers can be effected, for example, by fractional crystallization of salts of the anilinopropionic acid of the general formula XI with optically active bases, such as cinchonine or α-phenylethylamine, or by fractional crystallization of anilinobutyrolactones of the general formula XIa with optically active acids, such as, for example, D- or L-tartaric acid.

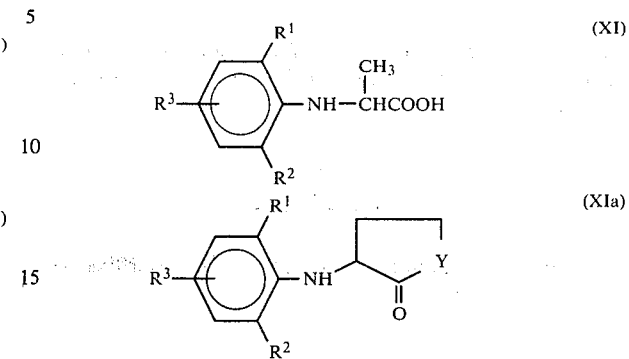

In the formulae XI and XIa, $R^1$, $R^2$, $R^3$ and Y are as defined for formula I.

However, a controlled synthesis starting from optically active halogenopropionic acid derivatives, such as, for example, methyl L-2-chloropropionate, optically active lactic acid ester-sulfonates or optically active halogenobutyrolactones and anilines of the general formula XII

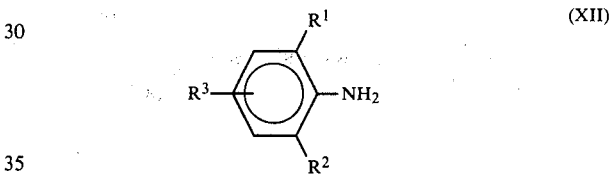

in which $R^1$, $R^2$ and $R^3$ are as defined for formula I, is also possible. This reaction chiefly takes place as an SN2 reaction, with inversion of the configuration. D-2-(2,6-Dimethylanilino)-propionic acid or its methyl ester are thus preferentially formed from 2,6-dimethylaniline and L-2-chloropropionic acid or methyl L-2-chloropropionate.

The agents according to the invention in general contain the active compounds of the formula I to the extent of about 2–95% by weight, preferably 5–90% by weight. They can be applied in the customary formulations as wettable powders, emulsifiable concentrates, atomizable solutions, dusting agents, dressing agents, dispersions, granules or microgranules.

Wettable powders are preparations which can be uniformly dispersed in water and which, in addition to the active compound and besides a diluent or inert substance, if appropriate, also contain wetting agents, for example polyoxyethylated alkylphenols, polyoxyethylated fatty alcohols, alkyl- or alkylphenyl-sulfonates, and dispersing agents, for example sodium lignin-sulfonate, sodium 2,2'-dinaphthylmethane-6,6'-disulfonate, sodium dibutylnaphthalenesulfonate or sodium oleoylmethyltauride. They are produced in the customary manner, for example by grinding and mixing the components.

Emulsifiable concentrates can be produced, for example, by dissolving the active compound in an inert organic solvent, for example butanol, cyclohexanone, dimethylformamide, xylene or higher-boiling aromatics or hydrocarbons, with the addition of one or more emulsifiers. In the case of liquid active compounds, it is also possible to dispense with all or some of the solvent content. Examples of emulsifiers which can be used are: calcium salts of alkylarylsulfonic acids, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitane-fatty acid esters, polyoxyethylenesorbitane fatty acid esters or polyoxyethylene sorbitol esters.

Dusting agents can be obtained by grinding the active compound with finely divided solid substances, for example talc, naturally occurring clays, such as kaolin, bentonite, pyrophillite or diatomaceous earth.

Granules can be produced either by atomizing the active compound onto an adsorbent, granular inert material, or by applying active compound concentrates onto the surface of carriers, such as sand or kaolinites, or of a granular inert material by means of binders, for example polyvinyl alcohol, sodium polyacrylate or mineral oils. Suitable active compounds can also be granulated in the manner customary for producing fertilizer granules, as a mixture with fertilizers if desired.

The active compound concentration in wettable powders is, for example, about 10 to 90% by weight and the remainder to make up to 100% by weight consists of customary formulation constituents. In the case of emulsifiable concentrates, the active compound concentration can be about 10 to 80% by weight. Dust-like formulations usually contain 5 to 20% by weight of active compound and atomizable solutions contain about 2 to 20% by weight.

The active compound content in granules depends partly on whether the active compound is in the liquid or solid form and on which granulation auxiliaries, fillers and the like are used.

The active compound formulations mentioned may also contain the adhesives, wetting agents, dispersing agents, emulsifying agents, penetration agents, solvents, fillers or carriers customary in each particular case.

For application, the concentrates, which are the commercially available form, are diluted, if necessary, in the customary manner, for example by means of water in the case of wettable powders, emulsifiable concentrates and dispersions, and sometimes also in the case of microgranules. Dust-like and granular formulations and atomizable solutions are not usually diluted with further inert substances before application.

Mixtures or mixed formulations with other pesticidal active compounds, such as, for example, insecticides, acaricides, herbicides, growth regulators or fungicides, are also possible, if desired. In some cases synergistic increases in the action can also be achieved, especially in mixtures with fungicides. The following compounds may be mentioned as examples of possible fungicidal partners in the mixture: elementary sulfur, ammonium polysulfide, sodium polysulfide, barium polysulfide, calcium polysulfide and calcium thiosulfate, calcium hypochlorite, boric acid, sodium tetraborate decahydrate (BORAX), zinc chloride, magnesium borate, nickel sulfate, potassium chromate, lead arsenate, cadmium chloride, cadmium carbonate, copper-I oxide (COPPER OXIDE), Bordeaux mixture, copper-II sulfate pentahydrate (COPPER SULFATE), basic copper-II chloride (COPPER OXYCHLORIDE), copper-II phosphate, tribasic copper-II sulfate (TRIBASIC COPPER SULFATE), basic copper-II carbonate (COPPER CARBONATE), copper-II dihydrazine-sulfate, cupramine complexes, a copper-II sulfate/ammonium carbonate mixture, a copper-II chloride/basic copper-II sulfate mixture, a basic copper-II carbonate/zinc salt mixture, the copper-II zinc chromate complex (COPPER ZINC CHROMATE), the copper-II zinc cadmium calcium chromate complex, the copper-II salt of oleic acid (COPPER OLEATE), copper-II salts of fatty acids, the copper-II salt of naphthenic acid, the copper-II salt of 8-hydroxyquinoline, the copper-II salt of 1,2-naphthoquinone 2-oxime, the copper-II salt of 3-phenylsalicylic acid, bis-(tri-n-butyl-tin)oxide, triphenyl-tin hydroxide (MENTIN HYDROXIDE), triphenyl-tin acetate (FENTIN ACETATE), bis-(tributyl-tin)succinate, mercury-I chloride (CALOMEL), mercury-II chloride, mercury-II oxide, the mercury zinc chromate complex, mercury-II lactate, ethyl-mercury chloride, 2-hydroxyethyl-mercury acetate, ethyl-mercury isothiocyanate, 3-ethoxypropyl-mercury bromide, chloromethoxypropyl-mercury acetate, methoxyethyl-mercury chloride, 2-methoxyethyl-mercury silicate, bis-(methyl-mercury)sulfate, bis-(methyl-mercury)-ammonium acetate, ethyl-mercury acetate, 2-methoxyethyl-mercury acetate, ethyl-mercury phosphate, isopropylmethyl-mercury acetate, methyl-mercury cyanide, methyl-mercury benzoate, N-cyano-N'-(methyl-mercury)-guanidine, methyl-mercury pentachlorophenolate, ethyl-mercury 2,3-dihydroxypropylmercaptide, methyl-mercury 8-hydroxyquinolate (Ortho LM), N-(methyl-mercury)-1,4,5,6,7,7-hexachlorobicyclo[2.2.1]-hept-5-ene-2,3-dicarboximide, N-(ethyl-mercury)-1,4,5,6,7,7-hexachlorobicyclo[2.2.1]hept-5-ene-2,3-dicarboximide, the sodium salt of ethyl-mercury-thiosalicylic acid, N-(ethyl-mercury)-p-toluenesulfonic acid anilide, phenyl-mercury acetate (PMA), phenyl-mercury propionate, phenyl-mercury-triethanolammonium lactate (PAS), phenyl-mercury-urea, N-(phenyl-mercury)-1,4,5,6,7,7-hexachlorobicyclo[2.2.1]hept-5-ene-2,3-dicarboximide, phenyl-mercury dimethyldithiocarbamate, phenyl-mercury formamide, phenyl-mercury chloride, phenyl-mercury benzoate, phenyl-mercury borate, phenyl-mercury hydroxide, phenyl-mercury iodide, basic phenyl-mercury nitrate, phenyl-mercury-monoethanolammonium lactate, phenyl-mercury salicylate, hydroxy-mercury-chlorophenol, hydroxy-mercury-trichlorophenol, hydroxy-mercury-nitrophenol, N-phenyl-mercury-ethylenediamine, phenyl-mercury-monoethanolammonium acetate, pyridyl mercury acetate, diphenyl-mercury 8-hydroxyquinolate, complexes of mercury-II with organic phosphates, a mixture of methyl-mercury 2,3-dihydroxypropylmercaptide and methyl-mercury acetate, a mixture of ethyl-mercury 2,3-dihydroxypropylmercaptide and ethyl-mercury acetate, a mixture of hydroxy-mercury-chlorophenol and hydroxy-mercury-nitrophenol, an organic complex of mercury and cadmium, cadmium succinate, cadmium di-n-propyl-xanthogenate, cadmium 8-hydroxyquinolate, phenylamino-cadmium acetate, phenylamino-cadmium dilactate, methylarsine sulfide, zinc octoate, zinc oleate, formalin, paraformaldehyde, acrolein, methyl bromide, methyl isothiocyanate, tetraiodoethylene, 1,3-dichloropropene and related chlorinated $C_3$-hydrocarbons, 1-chloro-3-bromoprop-1-ene, trans-1,4-dibromobut-2-ene, 1,3-dichloroprop-1-ene, 1-chloro-2-nitro propane, 2-chloro-1-nitropropane, trichloronitromethane, dichlorotetrafluoroacetone, the sodium salt of propionic acid, the calcium salt of propionic acid, bis-β-chloroethyl chlorofumarate, sorbic acid and its potassium salt, 2-propene-1,1-diol acetate, 2-aminobutane, dodecylguanidine acetate (dodine), dodecylguanidine phthalate, α-chloroacetyl-1,3-aminopropionitrile, α-bromoacetylvalinamide, 1,2-dichloro-1-(methylsulfonyl)-ethylene, 1,2-dichloro-1-(butylsulfonyl)-ethylene, trans-1,2-bis-(n-propylsulfonyl)-ethylene, p-dichlorobenzene, hexachlorobenzene (HCB), 1,2,4,5-tetrachloro-3-nitrobenzene (TECNAZENE), pentachloronitrobenzene (QUINTOZENE), 1,3,4-trichloro-2,5,6-trinitrobenzene, an isomer mixture of 1,3,4-trichloro-2,6-dinitrobenzene and 1,2,3-trichloro-4,6-dinitrobenzene, 2,4,5,6-tetrachloroisophthalic acid nitrile, 2,4-dinitrophenyl thiocyanate, diphenyl, o-nitrodiphenyl, 1-chloro-2,4-dinitronaphthalene, acenaphthene, 2,4,6-trichlorophenol, 2,4,5-trichlorophenol, 2,4,5-trichlorophenyl acetate, 2,4,5-trichlorophenyl chloroacetate, the zinc salt of trichlorophenol, m-cresyl acetate, 2,3,4,6-tetrachlorophenol, pentachlorophenol (PCP), o-dihydroxybenzene, 2,4-dihydroxy-n-hexylbenzene, 2-phenylphenol, 3,5-dibromosalicylaldehyde, 2-benzyl-4-chlorophenol, 2,2'-dihydroxy-5,5'-dichlorodiphenylmethane (DICHLOROPHEN), 2,2'-dihydroxy-3,3',5,5',6,6'-hexachloro-diphenylmethane, 2,2'-dihydroxy-5,5'-dichloro-diphenyl sulfide, 2,2'-dihydroxy-3,3',5,5'-tetrachloro-diphenyl sulfide, the disodium salt of 2,2'-dihydroxy-3,3',5,5'-tetrachloro-diphenyl sulfide, 4-chloro-o-phenylphenol, 1,4-dichloro-2,5-dimethoxybenzene (CHLORONEB), salicylanilide, bismuth salicylate, trifluoromethylsalicylanilide halogenated by chlorine or bromine, brominated salicyanilide, (3,5-dimethyl-4-chlorophenoxy)-ethanol, 2-(1-methyl-n-propyl)-4,6-dinitrophenyl 2-methylcrotonate (BINAPACRYL), 2-(1-methyl-n-propyl)-4,6-dinitrophenyl isopropyl carbonate (DINOBUTON), 2-(1-methyl-n-heptyl)-4,6-dinitrophenyl crotonate (DINOCAP), methyl 2,6-dinitro-4-(1-ethylhexyl)-phenyl carbonate+methyl 2,6-dinitro-4-(1-propyl-pentyl)-phenyl carbonate (DINOCTON), 4-nonyl-2,6-dinitro-phenyl butyrate, S-methyl 2-(1-methyl-n-heptyl)-4,6-dinitrophenyl thiocarbonate, 2,6-dichloro-4-nitroaniline (DICHLORAN), 2-cyanoethyl N-phenylcarbamate, propynyl N-phenylcarbamate, α-(2-bromoacetoxy)-acetanilide, 2,3,5,6-tetrachloro-1,4-benzoquinone (CHLORANIL), 2,3-dichloro-1,4-naphthoquinone (DICHLONE), 2-amino-3-chloro-1,4-naphthoquinone, 2-chloro-3-acetamino-1,4-naphthoquinone, 4-methyl-2,3,5,10-tetrahydro-3,5,10-trioxo-4H4-H-naphtho-(1,3-b)-1,4-triazine, 2,3,6,7-tetrachloro-4a-8a-epoxy-1,2,3,4,4a,8a-hexahydro-1,4-methanonaphthalene-5,8-dione, quinone oxime benzoyl hydrazone (BENQUINOX), N-(trichloromethylthio)-phthalimide (FOLPET), N-(trichloromethylthio)-cyclohex-4-ene-1,2-dicarboximide (CAPTAN), N-(1,1,2,2-tetrachloroethylthio)-cyclohex-4-ene-1,2-dicarboximide (CAPTAFOL), N-methanesulfonyl-N-trichloromethylthio-p-chloroaniline, N'-dichlorofluoromethylthio-N,N-dimethyl-N'-phenylsulfamide (DICHLORFLUAMID), S-(2-pyridyl 1-oxide) S'-trichloromethyl disulfide hydrochloride, O,O,O-trimethyl thiophosphate, O,O-diethyl phthalimidophosphonothioate, 5-amino-bis-(dimethylamido)-phosphinyl-3-phenyl-1,2,4-triazole (TRIAMIPHOS), 5-methylamino-bis-(dimethylamido)-phosphinyl-3-phenyl-1,2,4-triazole, O,O-diethyl O-2-pyrazinyl phosphorothioate, O-ethyl S,S-diphenyl dithiophosphate, O-ethyl S-benzyl phenyldithiophosphonate, O,O-diethyl S-benzyl thiolphosphate, the zinc salt of dithiocarbazinic acid, sodium N-methyl-dithiocarbamate (METHAM), sodium N-methoxyethyl-dithiocarbamate, sodium N,N-dimethyl-dithiocarbamate (DDC), ammonium N,N-dimethyl-dithiocarbamate; zinc N,N-dimethyl-dithiocarbamate (ZIRAM), iron N,N-dimethyl-dithiocarbamate (FERBAM), copper N,N-dimethyl-dithiocarbamate, disodium ethylene-1,2-bis-dithiocarbamate (NABAM), zinc ethylene-1,2-bis-dithiocarbamate (ZINEB), iron ethylene-1,2-bis-dithiocarbamate, manganese-II ethylene-1,2-bis-dithiocarbamate (MANEB), calcium ethylene-1,2-bis-dithiocarbamate, ammonium ethylene-1,2-bis-dithiocarbamate, zinc propylene-1,2-bis-dithiocarbamate (MEZINEB) (PROPINEB), bis(dimethylthiocarbamoyl) ethylene-1,2-bis-dithiocarbamate, the complex consisting of (MANEB) and the zinc salt (MANCOZEB), tetraethylthiuram monosulfide, bis-(N,N-dimethyldithiocarbamylmercapto)-methylarsine, tetramethylthiuram disulfide (THIRAM), dipyrrolidylthiuram disulfide, N,N'-bis-(dimethylamino)-thiuram disulfide, polyethylenethiuram sulfide, the complex consisting of (ZINEB) and polyethylenethiuram disulfide (METIRAM), bis-(3,4-dichloro-2(5H)-furanoyl) ether (mucochloric anhydride), 2-methoxymethyl-5-nitrofuran, 5-nitro-2-furfuraldoxime,5-nitro-2-furfurylamide oxime, 1-oxy-3-acetyl-6-methyl-cyclohex-5-ene-2,4-dione (dehydroacetic acid), 3-[2-(3,5-dimethyl-2-oxocyclohexyl)-2-hydroxyethyl]-glutarimide (cycloheximide), phthalimide, pyridine-2-thiol 1-oxide or 1-hydroxypyridine-2-thione, the zinc salt of pyridine-2-thiol 1-oxide, the manganese-II salt of pyridine-2-thiol 1-oxide, S-1-(1-oxido-2-pyridyl)-isothiuronium chloride, α,α-bis-(4-chlorophenyl)-3-pyridinemethanol (PARINOL), 8-hydroxyquinoline (8-QUINOLINOL), 8-hydroxyquinoline sulfate (QUINOSOL), benzoyl 8-hydroxyquinoline-salicylate, 3-(2-methylpiperidino)-propyl 3,4-dichlorobenzoate, 6-ethoxy-1,2-dihydro-2,2,4-trimethylquinoline (ETHOXYQUIN), N-laurylisoquinolinium bromide, 9-(p-n-hexyloxyphenyl)-10-methylacridinium chloride, 9-(p-n-hexyloxyphenyl)-10-methylacridinium p-toluenesulfonate, 2-n-heptadecylimidazolidine acetate (GLYODIN), 1-hydroxyethyl-2-heptadecylimidazolidine, 1-phenyl-3,5-dimethyl-4-nitrosopyrazole, 1-p-chlorophenyl-3,5-dimethyl-4-nitrosopyrazole, 1-p-sulfamylphenyl-3,5-dimethyl-4-nitrosopyrazole, N-(1-phenyl-2-nitropropyl)-piperazine, 2-dimethylamino-6-methyl-5-n-butyl-4-hydroxypyrimidine, N-dodecyl-1,4,5,6-tetrahydropyrimidine, N-dodecyl-2-methyl-1,4,5,6-tetrahydropyrimidine, 2-n-heptadecyltetrahydropyrimidine, 1-(4-amino-4-propyl-5-pyrimidyl-methyl)-2-methylpyridinium chloride hydrochloride, 2-(2'-furyl)-benzimidazole (FURIDAZOL), 3-dodecyl-1-methyl-2-phenylbenzimidazolium ferricyanide, methyl N-benzimidazol-2-yl-N-(butylcarbamoyl) carbamate (BENOMYL), 2-(o-chloroanilino)-4,6-dichloro-sym.-triazine, 2-ethylamino-6-methyl-5-n-butyl-4-hydroxypyrimidine, 5-chloro-4-phenyl-1,2-dithiol-3-one, 2,3-dicyano-1,4-dithia-anthraquinone (DITHIANONE), 2-(4-thiazolyl)-benzimidazole, 4-(2-chlorophenylhydrazono)-3-methyl-5-isoxazolone (DRAZOXOLON), thiazolidin-4-one-2-thione (RHODANINE), 3-(p-chlorophenyl)-5-methylrhodanine, 3,5-dimethyltetrahydro-1,3,5-thiadiazine-2-thione (DAZOMET), 3,3'-ethylene-bis-(tetrahydro-4,6-dimethyl)-2H-1,3,5-thiadiazine-2-thione) (MILNEB), 3-benzylideneamino-4-phenylthiazoline-2-thione, the zinc salt of 6-chlorobenzothiazole-2-thiol, 6,β-diethylaminoethoxy-2-dimethylamino-benzthiazole dihydrochloride, monoethanolammoniumbenzothiazole-2-thiol, laurylpyridinium 5-chloro-2-mercaptobenzothiazole, the zinc and sodium salts of 2-mercaptobenzothiazole and of dimethyldithiocarbamate, 6-(β-diethylaminoethoxy)-2-dimethylaminobenzothiazole dihydrochloride, 3-trichloromethylthiobenzothiazolone, 3-trichloromethylthiobenzoxazolone, 3-(trichloromethyl)-5-ethoxy-1,2,4-thiadiazole, 6-methyl-2-oxo-1,3-dithiolo[4,5-b]-quinoxaline (QUINOMETHIONAT), 2-thio-1,3-dithiolo[4,5-b]-quinoxaline (THIOQUINOX), 2,3-dihydro-5-carboxanilido-6-methyl-1,4-oxathiin, 3,3,4,4-tetrachlorotetrahydrothiophene 1,1-dioxide, 2,3-dihydro-5-carboxanilido-6-methyl-1,4-oxathiin 4,4-dioxide, ethyltrimethylammonium bromide, n-($C_{12}$, $C_{14}$ or $C_{16}$)-alkyl dimethylbenzylammonium chlorides, alkenyl-dimethylethylammonium bromides, dialkyldimethylammonium bromides, alkyldimethylbenzylammonium chlorides, ($C_9$–$C_{15}$)-alkyltolylmethyltrimethylammonium chlorides, di-isobutylcresoxyethoxyethyldimethylbenzylammonium chloride, p-diisobutylphenoxyethoxyethyldimethylbenzylammonium chloride, benzoyltrimethylammonium bromide, gliotoxin, 2,4-diguanidino-3,5,6-trihydroxycyclohexyl-5-deoxy-2-O-(2-deoxy-2-methylamino-α-L-glucopyranosyl)-3-C-formyl-β-L-lyxopentofuranoside (STREPTOMYCIN), 7-chloro-4,6-dimethoxycumaran-3-one-2-spiro-1'-(2'-methoxy-6'-methylcyclohex-2'-en-4'-one) (GRISEOFULVIN), 4-dimethylamino-1,4,4a,5,5a,6,11,12a-octahydro-3,5,6,10,12,12a-hexahydroxy-6-methyl-1,11-dioxo-2-naphthacene carboxamide (OXYTETRACYCLINE), 7-chloro-4-dimethylamino-1,4,4a,5,5a,6,11,12a-octahydro-3,6,10,12,12a-pentahydroxy-6-methyl-1,11-dioxo-2-naphthacenecarboxamide (CHLORTETRACYCLINE), (PIMARICIN), (LANDOMYCIN), (PHLEOMYCIN), (KASUGAMYCIN), (PHYTOACTIN), D(-)-threo-2,2-dichloro-N-[β-hydroxy-α-(hydroxymethyl)-p-nitrophenethyl]-acetamide (CHLORAMPHENICOL), blasticidin S-benzylamino-benzenesulfonate, N-(3-nitrophenyl)-itaconimide, phenoxyacetic acid, sodium p-dimethylamino-benzenediazosulfonate, acrolein-phenylhydrazone, 2-chloroacetaldehyde-(2,4-dinitrophenyl)-hydrazone, 2-chloro-3-(tolylsulfonyl)-propionitrile, 1-chloro-2-phenyl-pentane-4,5-diol-3-thione, the p-nonylphenoxy-polyethyleneoxyethanol-iodine complex, (α-nitromethyl)-o-chlorobenzylthioethylamine hydrochloride, 3-(p-t-butyl-phenylsulfonyl)-acrylonitrile, octachlorocyclohexenone, pentachlorobenzyl alcohol, pentachlorobenzyl acetate, pentachlorobenzaldehyde cyanohydrin, 2-norcamphanemethanol, 2,6-bis-(dimethylaminomethyl)-cyclohexanone, decachlorooctahydro-1,3,4-metheno-2H-cyclobuta[cd]-pentalen-2-one, 1-(3-chlorallyl)-3,5,7-triaza-1-azoniaadamantane chloride, coal tar and blast furnace tar, a mixture of nickel sulfate and maneb, a mixture of maneb and mercaptobenzothiazole, a mixture of zineb and mercaptobenzothiazole, a mixture of zineb and nickel-II chloride, a mixture of zineb and nickel-II sulfate, a mixture of ziram and basic copper sulfate, a mixture of ziram and zinc mercaptobenzothiazole, a mixture of thiram and cadmium chloride hydrate, a mixture of thiram and hydroxy-mercury-chlorophenol, a mixture of thiram and phenyl-mercury acetate, a mixture of polyethylene-bis-thiuram sulfide and copper oxychloride, a mixture of methylarsine bis-(dimethyldithiocarbamate), ziram and thiram, a mixture of folpet and phenyl-mercury acetate, a mixture of dodine, ferbam and sulfur, a mixture of dithianon and copper oxychloride, a mixture of dichlone, ferbam and sulfur, a mixture of dinocap and dinitrooctylphenol, a mixture of captan, quintozene and tribasic copper sulfate, a mixture of cadmium propionate and phenyl-mercury propionate, a formaldehyde/urea mixture, a mixture of phenylammonium cadmium dilactate and phenyl-mercury formamide and a mixture of basic copper sulfate and zinc salts.

The compounds claimed, of the formula I, are also suitable for use in the industrial field, for example as agents for protecting wood, in the paints sector or as preservatives, for example in cooling lubricants for metal working.

The invention is illustrated in more detail by the following examples:

A. PREPARATION EXAMPLES

EXAMPLE 1

Methyl 2-[N-(2,6-dimethylphenyl)-N-(ethoxythiocarbonylthioacetyl)-amino]-propionate 28.35 g of methyl 2-[N-(2,6-dimethylphenyl)-N-(chloroacetyl)-amino]-propionate and 15.0 g of sodium ethyl-xanthate are dissolved in 100 ml of acetone and the solution is stirred at 30° C. for 24 hours. Undissolved material is then filtered off and the filtrate is diluted with 300 ml of water and extracted with 100 ml of methylene chloride. The methylene chloride phase is separated off and dried over sodium sulfate and the methylene chloride is distilled off. 34.8 g (=94.5% of theory) of methyl 2-[N-(2,6-dimethylphenyl)-N-(ethoxythiocarbonylthioacetyl)-amino]-propionate are obtained as a light-colored oil with a refractive index $n_D^{22}$ of 1.5629.

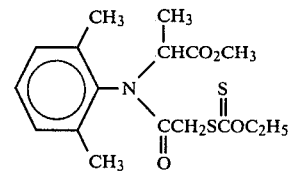

EXAMPLE 2

Methyl 2-[N-(2,6-dimethylphenyl)-N-(methoxythiocarbonylthioacetyl)-amino]-propionate 28.1 g of methyl 2-[N-(2,6-dimethylphenyl)-N-(mercaptoacetyl)-amino]-propionate (see Example 9) and 11.1 g of triethylamine are dissolved in 100 ml of toluene, and 12.1 g of O-methyl-thiocarbonyl chloride are added at 0° C. The mixture is then stirred at room temperature for 2 hours and at 40° C. for 1 hour. The precipitate of triethylamine hydrochloride is filtered off, the toluene phase is washed with water and dried over sodium sulfate and toluene is then distilled off under a waterpump vacuum. 31.9 g (=90% of theory) of methyl 2-[N-(2,6-dimethylphenyl)-N-(methoxythiocarbonylthioacetyl)-amino]-propionate are obtained as a yellow oil with a refractive index $n_D^{22}$ of 1.5681.

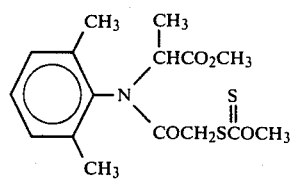

EXAMPLE 3

2-[N-(2,6-Dimethylphenyl)-N-(ethoxythiocarbonylthioacetyl)-amino]-butyrolactone 28.15 g of 2-[N-(2,6-dimethylphenyl)-N-(chloroacetyl)-amino]-butyrolactone and 15.2 g of sodium ethylxanthate are dissolved in 100 ml of acetone and the solution is left at 30° C. for 2 days. The salt precipitate is filtered off and the filtrate is diluted with 200 ml of water and extracted with methylene chloride. The methylene chloride phase is dried over sodium sulfate and the methylene chloride is distilled off. 34.1 g (=93% of theory) of 2-[N-(2,6-dimethylphenyl)-N-(ethoxythiocarbonylthioacetyl)-amino]-butyrolactone are obtained as a viscous yellow oil.

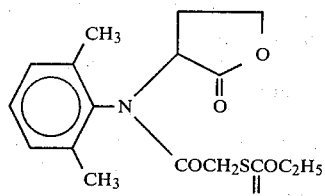

EXAMPLE 4 AD

D-{Methyl 2-[N-(ethoxycarbonylthioacetyl)-N-(2,6-dimethylphenyl)-amino]-propionate}

11.5 g (0.063 mole) of ethoxycarbonylthioacetyl chloride are added to 12.4 g (0.06 mole) of D-{methyl 2-[N-(2,6-dimethylphenyl)-amino]-propionate} in 60 ml of toluene at 90°–100° C. and the mixture is stirred at 100° C. until the evolution of gas has ended. After cooling, the mixture is neutralized with sodium bicarbonate solution, the toluene phase is separated off and dried over sodium sulfate and the toluene is distilled off. After recrystallization of the residue from toluene/cyclohexane, 18.9 g (85% of theory) of D-{methyl 2-[N-(2,6-dimethylphenyl)-N-(ethoxycarbonylthioacetyl)-amino]-propionate} with a melting point of 77° C. and an optical rotation $[\alpha_D]^{24°\ C.}$ of $-28.7°$ are obtained.

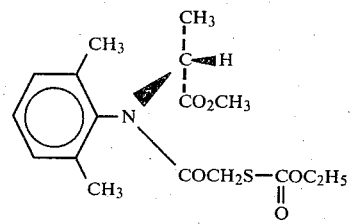

EXAMPLE 5

Methyl 2-[N-(5-aza-3-thia-5-cyano-4-methylthio-pent-4-eno-1-yl)-N-(2,6-dimethylphenyl)-amino]-propionate 28.35 g (0.1 mole) of methyl 2-[N-(chloroacetyl)-N-(2,6-dimethylphenyl)-amino]-propionate and 18.4 g (0.11 mole) of potassium S-monomethyl cyanimidothiocarbonate are stirred in 100 ml of acetonitrile at 60° C. for 12 hours. After filtering off the salt precipitate formed, the filtrate is diluted with ice and water and the solid formed is filtered off and recrystallized from toluene. 33 g (87% of theory) of methyl 2-[N-(5-aza-3-thia-5-cyano-4-methylthio-pent-4-eno-1-yl)-N-(2,6-dimethylphenyl)-amino]-propionate of melting point 109°–111° C. are obtained.

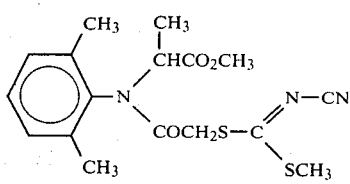

EXAMPLE 6

Methyl 2-[N-(methylaminothiocarbonylthioacetyl)-N-(2,6-dimethylphenyl)-amino]-propionate First 22.8 g (0.3 mole) of carbon disulfide and then 85.05 g (0.3 mole) of methyl 2-[N-(chloroacetyl)-N-(2,6-dimethylphenyl)-amino]-propionate are added to a solution of 18.56 g (0.6 mole) of methylamine in 300 ml of methanol at room temperature, and the mixture is then heated to 50°–60° C. for 8 hours. It is diluted with ice and water and the precipitate formed is filtered off and dried. 94.5 g (89% of theory) of methyl 2-[N-(methylaminothiocarbonylthioacetyl)-N-(2,6-dimethylphenyl)-amino]-propionate with a melting point of 119°–121° C. are obtained.

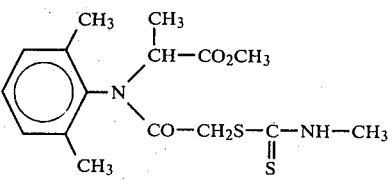

EXAMPLE 7

Methyl 2-[N-(5-aza-3-thia-4-ethylthio-hex-4-eno-1-yl)-N-(2,6-dimethylphenyl)-amino]-propionate 17.7 g (0.05 mole) of methyl 2-[N-(methylaminothiocarbonylthioacetyl)-N-(2,6-dimethylphenyl)-amino]-propionate, 9.6 g (0.06 mole) of ethyl iodide and 6.9 g (0.05 mole) of potassium carbonate are stirred in 60 ml of methanol at 55°–60° C. for 16 hours. After filtering off the salt precipitate, the filtrate is diluted with ice and water and extracted with methylene chloride. The methylene chloride phase is dried over sodium sulfate, the methylene chloride is distilled off and the semi-solid residue is recrystallized from isopropanol/water. 13.2 g (69% of theory) of methyl 2-[N-(5-aza-3-thia-4-ethylthio-hex-4-eno-1-yl)-N-(2,6-dimethylphenyl)-amino]-propionate with a melting point of 57.5°–58.5° C. are obtained.

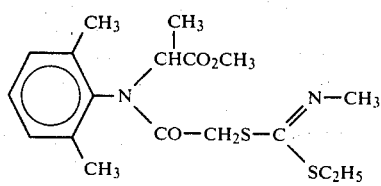

EXAMPLE 8

Methyl 2-[N-(acetylthioacetyl)-N-(2,6-dimethylphenyl)-amino]-propionate 12.1 g (0.12 mole) of triethylamine are added to 28.35 g (0.1 mole) of methyl 2-[N-(chloroacetyl)-N-(2,6-dimethylphenyl)-amino]-propionate and 9.1 g (0.12 mole) of thioacetic acid in 100 ml of acetonitrile, whilst cooling with ice, and the mixture is then subsequently stirred at 50° C. for 3 hours. After customary working up, the product is purified by distillation. 24.2 g (74.8% of theory) of methyl 2-[N-(acetylthioacetyl)-N-(2,6-dimethylphenyl)-amino]-propionate with a boiling point of 175°–178° C. under 0.025 mb are obtained.

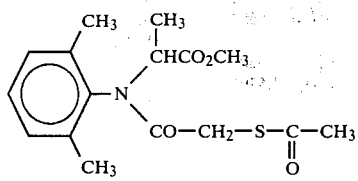

EXAMPLE 9

Methyl 2-[N-(mercaptoacetyl)-N-(2,6-dimethylphenyl)-amino]-propionate 25 g (0.0445 mole) of dithiodiglycolic acid bis-(N-1-methoxycarbonylethyl)-2,6-dimethylanilide (obtained by reacting methyl 2-(2,6-dimethylphenylamino)-propionate with dithiodiglycolic acid dichloride), 85 ml of water, 42.5 ml of concentrated hydrochloric acid and 200 ml of methanol are initially introduced into the reaction vessel and 20 g of zinc dust are added in portions at 0°–10° C. The mixture is then subsequently stirred for 3 hours, diluted with ice-water and extracted with methylene chloride. After drying the extract and distilling off the methylene chloride, 25 g (99.2% of theory) of virtually pure methyl 2-[N-(mercaptoacetyl)-N-(2,6-dimethylphenyl)-amino]-propionate with a melting point of 62.5°–63° C. are obtained.

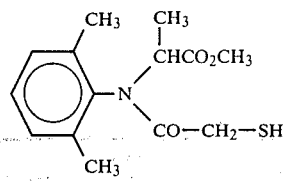

EXAMPLES 10 TO 152

Examples 10 to 152 for compounds of the formula I are listed in Tables 1 to 3 which follow, and in particular Examples 10 to 65 are given in Table 1, Examples 66 to 90 are given in Table 2 and Examples 91 to 152 are given in Table 3, and in addition to the individual substituents in the formula I and to the characteristic physico-chemical data for the products, the manner in which the compound of the formula I is prepared, analogously to one of the abovementioned Examples 1 to 9, is given in each case in the last column of the tables.

A selection of 14 further examples of optically active compounds of the formula I of the D-series is additionally listed in Table 4. These products are distinguished from the examples of the corresponding racemic products by the addition of the letters "AD" to the Example No. In Table 4, these optically active compounds are also characterized by their specific optical rotation $[\alpha]_D^t$, in addition to the corresponding substituents in the formula I, the manner in which they are prepared and the customary characteristic physico-chemical data.

TABLE 1

Formula I in which X denotes $-C\underset{O-R^7}{\overset{Y}{\parallel}}$ ; $R^3-\underset{R^2}{\overset{R^1}{\underset{|}{\bigcirc}}}-N\underset{CCH_2S-\underset{O}{\overset{Y}{\parallel}}-OR^7}{\overset{R}{\diagdown}}$

| Example No. | $R^1$ | $R^2$ | $R^3$ | R | Y | $R^7$ | Melting point/ boiling point/ $n_D$ | Preparation analogous to Example No. |
|---|---|---|---|---|---|---|---|---|
| 10 | —CH₃ | —CH₃ | —H | CH₃<br>\|<br>—CHCO₂CH₃ | S | -i-C₃H₇ | $n_D^{22} = 1.5529$ | 1 |
| 11 | —CH₃ | —CH₃ | —H | " | S | -n-C₃H₇ | $n_D^{20} = 1.5570$ | 1 |
| 12 | —CH₃ | —CH₃ | —H | " | S | -s-C₄H₉ | $n_D^{20} = 1.5542$ | 1 |
| 13 | —CH₃ | —CH₃ | —H | " | S | -i-C₄H₉ | $n_D^{24} = 1.5505$ | 1 |
| 14 | —CH₃ | —CH₃ | —H | " | S | -n-C₅H₉ | | 1 |
| 15 | —CH₃ | —CH₃ | —H | " | S | —⟨H⟩ | $n_D^{15} = 1.5669$ | 1 |
| 16 | —CH₃ | —CH₃ | —H | " | S | —CH₂CH₂OCH₃ | Melting point: 60–62° C. | 1 |
| 17 | —CH₃ | —CH₃ | —H | " | S | —CH₂CH=CH₂ | | 1 |
| 18 | —CH₃ | —CH₃ | —H | " | S | —CH₂C≡CH | | 1 |
| 19 | —CH₃ | —CH₃ | —H | " | O | —C₂H₅ | Melting point 76–78° C. | 2 |
| 20 | —CH₃ | —CH₃ | —H | " | O | —CH₃ | Melting point 77.5–79° C. | 4 AD |
| 21 | —CH₃ | —CH₃ | —H | " | S | —C₂H₅ | $n_D^{17} = 1.5612$ | 1 |
| 22 | —C₂H₅ | —C₂H₅ | —H | " | S | —C₂H₅ | $n_D^{20} = 1.5600$ | 1 |
| 23 | -i-C₃H₇ | H | —H | " | S | —C₂H₅ | Melting point: 83° C. | 1 |
| 24 | -i-C₃H₇ | H | —H | " | S | -i-C₃H₇ | $n_D^{18} = 1.5516$ | 1 |

TABLE 1-continued

Formula I in which X denotes $-\overset{Y}{\underset{O-R^7}{\overset{\|}{C}}}$ ; $R^3 \longrightarrow \underset{R^2}{\overset{R^1}{\bigcirc}} \underset{}{N} \overset{R}{\underset{CCH_2S-\overset{Y}{\underset{}{\overset{\|}{C}}}-OR^7}{}}$

| Example No. | $R^1$ | $R^2$ | $R^3$ | R | Y | $R^7$ | Melting point/ boiling point/ $n_D$ | Preparation analogous to Example No. |
|---|---|---|---|---|---|---|---|---|
| 25 | —CH₃ | —CH₃ | 3-CH₃ | " | S | —C₂H₅ | 1 | 1 |
| 26 | —CH₃ | —H | —H | —CH₂CO₂CH₃ | S | —C₂H₅ | $n_D^{24} = 1.5665$ | 1 |
| 27 | -i-C₃H₇ | —H | —H | " | S | —C₂H₅ | $n_D^{22} = 1.5602$ | 1 |
| 28 | —CH₃ | —H | 4-CH₃ | " | S | —C₂5 | $n_D^{19} = 1.5600$ | 1 |
| 29 | —CH₃ | —H | 3-CH₃ | " | S | —C₂H₅ | $n_D^{23.5} = 1.5670$ | 1 |
| 30 | —CH₃ | —CH₃ | —H | " | S | —C₂H₅ | $n_D^{24} = 1.5681$ | 1 |
| 31 | —CH₃ | —CH₃ | —H | " | O | —CH₃ | $n_D^{24} = 1.5392$ | 4 AD |
| 32 | —CH₃ | —CH₃ | —H | " | O | —C₂H₅ | | 4 AD |
| 33 | —CH₃ | —CH₃ | —H | —CH₂CO₂C₂H₅ | S | —C₂H₅ | $n_D^{22} = 1.5608$ | 1 |
| 34 | —Cl | —CH₃ | —H | —CH₂CO₂CH₃ | S | —C₂H₅ | $n_D^{17} = 1.5796$ | 1 |
| 35 | —CH₃ | —CH₃ | —H | 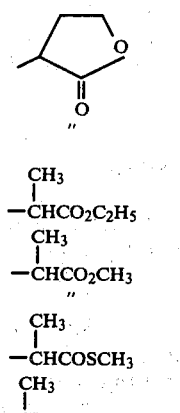 | S | —CH₃ | | 3 |
| 36 | —CH₃ | —CH₃ | —H | " | S | -i-C₃H₇ | Melting point: 95–96° C. | 3 |
| 37 | —CH₃ | —CH₃ | —H | —CHCO₂C₂H₅ with CH₃ | S | —C₂H₅ | $n_D^{23.5} = 1.5516$ | 1 |
| 38 | —CH₃ | —Cl | —H | —CHCO₂CH₃ with CH₃ | S | -n-C₃H₇ | $n_D^{21} = 1.5648$ | 1 |
| 39 | —CH₃ | —Cl | —H | " | S | -i-C₃H₇ | $n_D^{21} = 1.5644$ | 1 |
| 40 | —CH₃ | —CH₃ | —H | —CHCOSCH₃ with CH₃ | S | —C₂H₅ | | 1 |
| 41 | —CH₃ | —CH₃ | —H | —CHCO—SCH₃ with CH₃ | S | —CH₃ | | 2 |
| 42 | —CH₃ | —Cl | —H | —CHCO₂CH₃ with CH₃ | O | —CH₃ | $n_D^{24} = 1.5413$ | 4 AD |
| 43 | —CH₃ | —CH₃ | —H | —CHCO₂N(CH₃)₂ with CH₃ | S | —C₂H₅ | | 1 |
| 44 | —C₂H₅ | —C₂H₅ | —H | —CH₂CO₂C₂H₅ | S | —C₂H₅ | | 1 |
| 45 | —CH₃ | —C₂H₅ | —H | —CHCO₂CH₃ with CH₃ | S | -n-C₃H₇ | $n_D^{21} = 1.5568$ | 1 |
| 46 | —CH₃ | —C₂H₅ | —H | —CHCO₂CH₃ with CH₃ | S | -i-C₃H₇ | $n_D^{20} = 1.5569$ | 1 |
| 47 | —CH₃ | —CH₃ | —H | —CHCO₂C₂H₅ with CH₃ | S | -i-C₃H₇ | $n_D^{23.5} = 1.5495$ | 1 |
| 48 | —CH₃ | —Cl | —H | —CHCO₂CH₃ with CH₃ | S | —C₂H₅ | $n_D^{17} = 1.5796$ | 1 |
| 49 | —CH₃ | —Cl | —H | " | S | —CH₃ | | 2 |
| 50 | —CH₃ | —C₂H₅ | —H | " | O | —C₂H₅ | Melting point: 73–76° C. | 4 AD |
| 51 | —CH₃ | —C₂H₅ | —H | " | O | —CH₃ | Melting point 86–89° C. | |
| 52 | —CH₃ | —Cl | —H | —CH₂CO₂CH₃ | O | —C₂H₅ | $n_D^{24} = 1.5387$ | 4 AD |
| 53 | —CH₃ | —CH₃ | —H | —CHCO₂C₂H₅ with CH₃ | O | —CH₃ | | 4 AD |
| 54 | —CH₃ | —H | —H | —CHCO₂CH₃ with CH₃ | O | —CH₃ | $n_D^{20} = 1.5329$ | 4 AD |
| 55 | —CH₃ | —H | 3-CH₃ | " | O | —CH₃ | $n_D^2 = 1.5350$ | 4 AD |
| 56 | —C₂H₅ | —C₂H₅ | —H | " | O | —CH₃ | $n_D^{20} = 1.5313$ | 4 AD |
| 57 | —CH₃ | —CH₃ | —H | 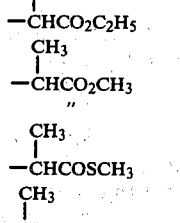 | O | —CH₃ | | 4 AD |
| 58 | —CH₃ | —CH₃ | —H | " | O | —C₂H₅ | | 4 AD |

TABLE 1-continued

Formula I in which X denotes $-\overset{Y}{\underset{O-R^7}{C}}$ ; $R^3-\text{[phenyl with } R^1, R^2\text{]}-N(R)-COCH_2S-\overset{Y}{\underset{}{C}}-OR^7$

| Example No. | $R^1$ | $R^2$ | $R^3$ | R | Y | $R^7$ | Melting point/boiling point/$n_D$ | Preparation analogous to Example No. |
|---|---|---|---|---|---|---|---|---|
| 59 | $-CH_3$ | $-CH_3$ | $-H$ | (tetrahydrothiophene-2-carbonyl, S in ring, C=O) | O | $-CH_3$ | | 4 AD |
| 60 | $-CH_3$ | $-CH_3$ | $-H$ | " | S | $-C_2H_5$ | | 1 |
| 61 | $-CH_3$ | $-CH_3$ | $-H$ | " | S | $-CH_3$ | | 2 |
| 62 | $-CH_3$ | $-CH_3$ | $-H$ | $-CHCO_2CH_3$ with $CH_3$ | O | $-i\text{-}C_3H_7$ | | 4 AD |
| 63 | $-CH_3$ | $-CH_3$ | $-H$ | " | O | $-n\text{-}C_3H_7$ | | 4 AD |
| 64 | $-CH_3$ | $-CH_3$ | $-H$ | " | O | $-s\text{-}C_4H_9$ | | 4 AD |
| 65 | $-CH_3$ | $-CH_3$ | $-H$ | " | O | $-CH_2CH_2OCH_3$ | | 4 AD |

TABLE 2

Formula I in which X denotes $-\overset{N-CN}{\underset{SR^7}{C}}$ ; $R^3-\text{[phenyl with } R^1, R^2\text{]}-N(R)-COCH_2S-\overset{N-CN}{\underset{SR^7}{C}}$

| Example No. | $R^1$ | $R^2$ | $R^3$ | R | $R^7$ | Characteristic physico-chemical data | Preparation analogous to Example No. |
|---|---|---|---|---|---|---|---|
| 66 | $-CH_3$ | $-CH_3$ | $-H$ | (3-methyl-γ-butyrolactone) | $-CH_3$ | | 5 |
| 67 | $-CH_3$ | $-CH_3$ | $-H$ | (3-methyl-γ-butyrolactone) | $-C_2H_5$ | | 5 |
| 68 | $-CH_3$ | $-CH_3$ | $-H$ | $-CH_2CO_2CH_3$ | $-CH_3$ | Melting point: 90° C. | 5 |
| 69 | $-CH_3$ | $-H$ | 3-$CH_3$ | $-CH_2CO_2CH_3$ | $-CH_3$ | viscous oil | 5 |
| 70 | $-CH_3$ | $-CH_3$ | $-H$ | $-CH_2CO_2CH_3$ | $-C_2H_5$ | | 5 |
| 71 | $-CH_3$ | $-CH_3$ | $-H$ | $-CHCO_2CH_3$ with $CH_3$ | $-C_2H_5$ | Melting point: 106–107° C. | 5 |
| 72 | $-CH_3$ | $-CH_3$ | $-H$ | $-CHCO_2CH_3$ with $CH_3$ | $-n\text{-}C_3H_7$ | | 5 |
| 73 | $-CH_3$ | $-CH_3$ | $-H$ | $-CHCO_2CH_3$ with $CH_3$ | $-i\text{-}C_3H_7$ | | 5 |
| 74 | $-CH_3$ | $-CH_3$ | $-H$ | $-CHCO_2CH_3$ with $CH_3$ | $-CH_2CH=CH_2$ | | 5 |
| 75 | $-CH_3$ | $-CH_3$ | $-H$ | $-CHCO_2CH_3$ with $CH_3$ | $-CH_2C\equiv CH$ | | 5 |
| 76 | $-CH_3$ | $-CH_3$ | $-H$ | $-CHCO_2CH_3$ with $CH_3$ | cyclopentyl | | 5 |
| 77 | $-CH_3$ | $-CH_3$ | $-H$ | $-CHCO_2C_2H_5$ with $CH_3$ | $-CH_3$ | Melting point: 97–99° C. | 5 |

TABLE 2-continued

Formula I in which X denotes $-C\begin{subarray}{c}N-CN\\ \diagdown SR^7\end{subarray}$ $R^3-\underset{R^2}{\underset{|}{\overset{R^1}{\underset{|}{\bigcirc}}}}-N\underset{COCH_2S-C}{\overset{R}{\diagup}}\begin{subarray}{c}N-CN\\ \diagdown SR^7\end{subarray}$

| Example No. | $R^1$ | $R^2$ | $R^3$ | R | $R^7$ | Characteristic physico-chemical data | Preparation analogous to Example No. |
|---|---|---|---|---|---|---|---|
| 78 | $-CH_3$ | $-CH_3$ | $-H$ | (tetrahydrothiophen-3-yl, 2-oxo) | $-CH_3$ | | 5 |
| 79 | $-CH_3$ | $-CH_3$ | $-H$ | (tetrahydrothiophen-3-yl, 2-oxo) | $-C_2H_5$ | | 5 |
| 80 | $-CH_3$ | $-CH_3$ | $-H$ | $-\underset{\underset{CHCOSCH_3}{\mid}}{CH_3}$ | $-CH_3$ | | 5 |
| 81 | $-CH_3$ | $-Cl$ | $-H$ | $-CH_2CO_2CH_3$ | $-CH_3$ | | 5 |
| 82 | $-CH_3$ | $-Cl$ | $-H$ | $-CH_2CO_2CH_3$ | $-C_2H_5$ | | 5 |
| 83 | $-C_2H_5$ | $-CH_3$ | $-H$ | $-CH_2CO_2CH_3$ | $-CH_3$ | | 5 |
| 84 | $-CH_3$ | $-Cl$ | $-H$ | $-\underset{\underset{CHCO_2CH_3}{\mid}}{CH_3}$ | $-CH_3$ | viscous oil | 5 |
| 85 | $-CH_3$ | $-Cl$ | $-H$ | $-\underset{\underset{CHCO_2CH_3}{\mid}}{CH_3}$ | $-C_2H_5$ | | 5 |
| 86 | $-C_2H_5$ | $-CH_3$ | $-H$ | $-\underset{\underset{CHCO_2CH_3}{\mid}}{CH_3}$ | $-CH_3$ | viscous oil | 5 |
| 87 | $-C_2H_5$ | $-CH_3$ | $-H$ | $-\underset{\underset{CHCO_2CH_3}{\mid}}{CH_3}$ | $-C_2H_5$ | | 5 |
| 88 | $-CH(CH_3)_2$ | $-H$ | $-H$ | $-\underset{\underset{CHCO_2CH_3}{\mid}}{CH_3}$ | $-CH_3$ | $n_D^{22}=1.5710$ | 5 |
| 89 | $-CH_3$ | $-H$ | $-H$ | $-CH_2CO_2CH_3$ | $-CH_3$ | viscous oil | 5 |
| 90 | $-CH_3$ | $-CH_3$ | $-H$ | $-\underset{\underset{CHCO_2CH(CH_3)_2}{\mid}}{CH_3}$ | $-CH_3$ | $n_D^{19}=1.5590$ | 5 |

TABLE 3

Formula I: $R^3-\underset{R^2}{\underset{|}{\overset{R^1}{\underset{|}{\bigcirc}}}}-N\underset{COCH_2S-X}{\overset{R}{\diagup}}$

| Example No. | $R^1$ | $R^2$ | $R^3$ | R | X | Characteristic physico-chemical data | Preparation analogous to Example No. |
|---|---|---|---|---|---|---|---|
| 91 | $-CH_3$ | $-CH_3$ | $-H$ | $-\underset{\underset{CO_2CH_3}{\mid}}{CH}-CH_3$ | $-\overset{\overset{S}{\parallel}}{C}-S-C_2H_5$ | $n_D^{20}=1.5612$ | 1 |
| 92 | $-CH_3$ | $-CH_3$ | $-H$ | " | $-\overset{\overset{S}{\parallel}}{C}-SCH_3$ | | 1 |
| 93 | $-CH_3$ | $-Cl$ | $-H$ | " | $-\overset{\overset{S}{\parallel}}{C}-SC_2H_5$ | | 1 |
| 94 | $-CH_3$ | $-CH_3$ | $-H$ | " | $-\overset{\overset{O}{\parallel}}{C}-SC(CH_3)_3$ | | 2 |
| 95 | $-CH_3$ | $-CH_3$ | $-H$ | $-CH_2CO_2CH_3$ | $-\overset{\overset{S}{\parallel}}{C}-SC_2H_5$ | | 1 |

TABLE 3-continued

Formula I: $R^3$—(phenyl with $R^1$, $R^2$)—N(R)—COCH$_2$S—X

| Example No. | $R^1$ | $R^2$ | $R^3$ | R | X | Characteristic physico-chemical data | Preparation analogous to Example No. |
|---|---|---|---|---|---|---|---|
| 96 | —CH$_3$ | —CH$_3$ | —H | 3-(tetrahydrofuran-2-one-yl) | —C(=S)—SC$_2$H$_5$ | $n_D^{20} = 1.6086$ | 1 |
| 97 | —CH$_3$ | —CH$_3$ | —H | 3-(tetrahydrothiophen-2-one-yl) | —C(=S)—SC$_2$H$_5$ | | 1 |
| 98 | —CH$_3$ | —CH$_3$ | —H | —CH(CH$_3$)CO$_2$CH$_3$ | —C(=O)—SC$_2$H$_5$ | | 2 |
| 99 | —CH$_3$ | —CH$_3$ | —H | " | —C(=O)—SCH$_3$ | | 2 |
| 100 | —CH$_3$ | —CH$_3$ | —H | 3-(tetrahydrothiophen-2-one-yl) | —C(=O)—SC$_2$H$_5$ | | 4 AD |
| 101 | —CH$_3$ | —CH$_3$ | —H | —CH(CH$_3$)CO$_2$CH$_3$ | —C(=O)—NH—CH$_3$ | Melting point: 114–115° C. | 2 |
| 102 | —CH$_3$ | —CH$_3$ | —H | " | —C(=O)—NH—C$_2$H$_5$ | Melting point: 141–142.5° C. | 2 |
| 103 | —CH$_3$ | —CH$_3$ | —H | " | —C(=O)—NH—C$_4$H$_9$(n) | Melting point: 99–100° C. | 2 |
| 104 | —CH$_3$ | —CH$_3$ | —H | " | —C(=O)—N(CH$_3$)$_2$ | Melting point: 124.5–125.5° C. | 2 |
| 105 | —CH$_3$ | —CH$_3$ | —H | " | —C(=O)—N(C$_2$H$_5$)$_2$ | $n_D^{20} = 1.5336$ | 2 |
| 106 | —CH$_3$ | —CH$_3$ | —H | 3-(tetrahydrofuran-2-one-yl) | —C(=O)—NH—CH$_3$ | | 2 |
| 107 | —CH$_3$ | —CH$_3$ | —H | " | —C(=O)—N(CH$_3$)$_2$ | | 2 |
| 108 | —CH$_3$ | —CH$_3$ | —H | 3-(tetrahydrothiophen-2-one-yl) | —C(=O)—NH—CH$_3$ | | 2 |
| 109 | —CH$_3$ | —CH$_3$ | —H | " | —C(=O)—N(CH$_3$)$_2$ | | 2 |
| 110 | —CH$_3$ | —CH$_3$ | —H | 3-(tetrahydrofuran-2-one-yl) | —C(=S)—NH—CH$_3$ | | 6 |
| 111 | —CH$_3$ | —CH$_3$ | —H | 3-(tetrahydrothiophen-2-one-yl) | —C(=S)—NH—CH$_3$ | | 6 |
| 112 | —CH$_3$ | —CH$_3$ | —H | —CH(CH$_3$)—COSCH$_3$ | —C(=O)—NH—CH$_3$ | | 2 |

TABLE 3-continued

Formula I: $R^3 \underset{R^2}{\overset{R^1}{\diagdown}} \!\!-\!\! N(R)(COCH_2S\!-\!X)$ (aryl with $R^1, R^2, R^3$)

| Example No. | $R^1$ | $R^2$ | $R^3$ | R | X | Characteristic physico-chemical data | Preparation analogous to Example No. |
|---|---|---|---|---|---|---|---|
| 113 | $-CH_3$ | $-CH_3$ | $-H$ | " | $-\overset{S}{\underset{\|}{C}}-NH-CH_3$ | | 6 |
| 114 | $-CH_3$ | $-CH_3$ | $-H$ | " | $-\overset{O}{\underset{\|}{C}}-N(CH_3)_2$ | | 2 |
| 115 | $-CH_3$ | $-CH_3$ | $-H$ | $-\overset{CH_3}{\underset{\|}{CH}}-CO_2CH_3$ | $-\overset{S}{\underset{\|}{C}}-NH-C_2H_5$ | Melting point: 113–114° C. | 6 |
| 116 | $-CH_3$ | $-CH_3$ | $-H$ | " | $-\overset{S}{\underset{\|}{C}}-NH-C_3H_7(i)$ | Melting point: 107.5–108.5° C. | 6 |
| 117 | $-CH_3$ | $-CH_3$ | $-H$ | " | $-\overset{S}{\underset{\|}{C}}-NH-C_4H_9(n)$ | Melting point: 104–105° C. | 6 |
| 118 | $-CH_3$ | $-CH_3$ | $-H$ | " | $-\overset{S}{\underset{\|}{C}}-NH-C_3H_7(n)$ | Melting point: 120–120.5° C. | 6 |
| 119 | $-CH_3$ | $-CH_3$ | $-H$ | " | $-\overset{S}{\underset{\|}{C}}-NH-C_4H_9(i)$ | Melting point: 126–127° C. | 6 |
| 120 | $-CH_3$ | $-CH_3$ | $-H$ | " | $-\overset{S}{\underset{\|}{C}}-NH-C_4H_9(t)$ | $n_D^{25.5} = 1.5465$ | 6 |
| 121 | $-CH_3$ | $-CH_3$ | $-H$ | " | $-\overset{S}{\underset{\|}{C}}-NH-CH_2-\text{furyl}$ | Melting point: 117–119° C. | 6 |
| 122 | $-CH_3$ | $-CH_3$ | $-H$ | " | $-\overset{S}{\underset{\|}{C}}-NH-CH_2CH_2OCH_3$ | Melting point: 80–81° C. | 6 |
| 123 | $-CH_3$ | $-CH_3$ | $-H$ | " | $-\overset{S}{\underset{\|}{C}}-NH-CH_2CH=CH_2$ | Melting point: 116–118° C. | 6 |
| 124 | $-CH_3$ | $-CH_3$ | $-H$ | " | $-C(=N-CH_3)(SCH_3)$ | $n_D^{20} = 1.5412$ | 7 |
| 125 | $-CH_3$ | $-CH_3$ | $-H$ | " | $-C(=N-C_2H_5)(SCH_3)$ | $n_D^{26} = 1.5349$ | 7 |
| 126 | $-CH_3$ | $-CH_3$ | $-H$ | " | $-C(=N-C_2H_5)(SC_2H_5)$ | $n_D^{26} = 1.5363$ | 7 |
| 127 | $-CH_3$ | $-CH_3$ | $-H$ | " | $-C(=N-C_3H_7-(i))(SCH_3)$ | | 7 |
| 128 | $-CH_3$ | $-CH_3$ | $-H$ | " | $-C(=N-C_3H_7-(i))(SC_2H_5)$ | $n_D^{26} = 1.5286$ | 7 |
| 129 | $-CH_3$ | $-CH_3$ | $-H$ | " | $-C(=N-C_3H_7-(n))(SCH_3)$ | $n_D^{26} = 1.5256$ | 7 |
| 130 | $-CH_3$ | $-CH_3$ | $-H$ | " | $-C(=N-C_4H_9-(n))(SCH_3)$ | $n_D^{20} = 1.5528$ | 7 |

TABLE 3-continued

Formula I: 
$$R^3 \text{—} \underset{R^2}{\underset{|}{\overset{R^1}{\overset{|}{C_6H_3}}}} \text{—} N(R)(COCH_2S\text{—}X)$$

| Example No. | $R^1$ | $R^2$ | $R^3$ | R | X | Characteristic physico-chemical data | Preparation analogous to Example No. |
|---|---|---|---|---|---|---|---|
| 131 | —CH$_3$ | —CH$_3$ | —H | —CH(CH$_3$)CO—SCH$_3$ | —C(=N—CH$_3$)SCH$_3$ | | 7 |
| 132 | —CH$_3$ | —CH$_3$ | —H | γ-butyrolactone-α-yl | —C(=N—CH$_3$)SCH$_3$ | | 7 |
| 133 | —CH$_3$ | —CH$_3$ | —H | γ-thiobutyrolactone-α-yl | —C(=N—CH$_3$)SCH$_3$ | | 7 |
| 134 | —CH$_3$ | —C$_2$H$_5$ | —H | —CH(CH$_3$)CO$_2$CH$_3$ | —C(=S)NH—CH$_3$ | $n_D^{22.5}$ = 1.5454 | 6 |
| 135 | —C$_3$H$_7$—(i) | —H | —H | " | " | Melting point: 125–127° C. | 6 |
| 136 | —C$_2$H$_5$ | —C$_2$H$_5$ | —H | —CH$_2$CO$_2$C$_2$H$_5$ | " | Melting point: 67–69° C. | 6 |
| 137 | —CH$_3$ | —CH$_3$ | —H | —CH$_2$—CO$_2$CH$_3$ | —C(=O)—NH—CH$_3$ | | 2 |
| 138 | —CH$_3$ | —CH$_3$ | —H | " | —C(=O)—N(CH$_3$)$_2$ | | 2 |
| 139 | —CH$_3$ | —CH$_3$ | —H | " | —C(=S)—NH—CH$_3$ | | 6 |
| 140 | —CH$_3$ | —CH$_3$ | —H | " | —C(=N—CH$_3$)SCH$_3$ | | 7 |
| 141 | —CH$_3$ | —CH$_3$ | —H | —CH(CH$_3$)CO$_2$CH$_3$ | —C(=O)—H | | 2 |
| 142 | —CH$_3$ | —CH$_3$ | —H | " | —C(=O)—C$_2$H$_5$ | | 2 |
| 143 | —CH$_3$ | —CH$_3$ | —H | γ-butyrolactone-α-yl | —H | | 9 |
| 144 | —CH$_3$ | —CH$_3$ | —H | γ-thiobutyrolactone-α-yl | —H | | 9 |
| 145 | —CH$_3$ | —CH$_3$ | —H | —CH$_2$—CO$_2$CH$_3$ | —C(=O)—H | | 2 |
| 146 | —CH$_3$ | —CH$_3$ | —H | " | —C(=O)—CH$_3$ | | 2 |
| 147 | —CH$_3$ | —CH$_3$ | —H | γ-butyrolactone-α-yl | —C(=O)—H | | 2 |

TABLE 3-continued

Formula I:

| Example No. | R¹ | R² | R³ | R | X | Characteristic physico-chemical data | Preparation analogous to Example No. |
|---|---|---|---|---|---|---|---|
| 148 | $-CH_3$ | $-CH_3$ | $-H$ | (tetrahydrothiophen-2-one-3-yl) | $-\overset{O}{\underset{\|}{C}}-H$ | | 2 |
| 149 | $-CH_3$ | $-CH_3$ | $-H$ | $-\underset{\underset{CH_3}{\|}}{CH}-COSCH_3$ | $-\overset{O}{\underset{\|}{C}}-H$ | | 2 |
| 150 | $-CH_3$ | $-CH_3$ | $-H$ | $-CH_2-CO_2CH_3$ | $-H$ | | 9 |
| 151 | $-CH_3$ | $-CH_3$ | $-H$ | $-\underset{\underset{CO_2CH_3}{\|}}{CH}-CH_3$ | $-C\overset{N-CH_2CH_2CH_3}{\underset{SC_2H_5}{\diagup}}$ | $n_D^{26.5} = 1.5331$ | 7 |
| 152 | $-CH_3$ | $-CH_3$ | $-H$ | '' | $-\underset{\underset{O}{\|}}{C}-CH_2SCH_3$ | | 2 |

TABLE 4

Optically active compounds

Formula I in which R denotes $-\underset{\underset{CH_3}{\|}}{CH}-COR^5$:

| Example No. | R¹ | R² | R³ | R⁵ | X | Characteristic physico-chemical data | Specific optical rotation $[\alpha]_D^{t°C.}$ | Preparation analogous to Example No. |
|---|---|---|---|---|---|---|---|---|
| 1 AD | $-CH_3$ | $-CH_3$ | $-H$ | $-OCH_3$ | $-\underset{\underset{S}{\|}}{C}-OC_2H_5$ | $n_D^{21} = 1.5630$ | $[\alpha]_D^{20°C.} = -24.56°$ | 1 |
| 10 AD | $-CH_3$ | $-CH_3$ | $-H$ | $-OCH_3$ | $-\underset{\underset{S}{\|}}{C}-OCH(CH_3)_2$ | $n_D^{20} = 1.5526$ | $[\alpha]_D^{22°C.} = -27.46°$ | 1 |
| 9 AD | $-CH_3$ | $-CH_3$ | $-H$ | $-OCH_3$ | $-H$ | | | 9 |
| 5 AD | $-CH_3$ | $-CH_3$ | $-H$ | $-OCH_3$ | $-C\overset{N-CN}{\underset{SCH_3}{\diagup}}$ | | | 5 |
| 6 AD | $-CH_3$ | $-CH_3$ | $-H$ | $-OCH_3$ | $-\underset{\underset{S}{\|}}{C}-NH-CH_3$ | | | 6 |
| 124 AD | $-CH_3$ | $-CH_3$ | $-H$ | $-OCH_3$ | $-C\overset{N-CH_3}{\underset{SCH_3}{\diagup}}$ | | | 7 |
| 53 AD | $-CH_3$ | $-CH_3$ | $-H$ | $-OC_2H_5$ | $-\underset{\underset{O}{\|}}{C}-OCH_3$ | | $[\alpha]_D^{24°C.} = -32.53°$ | 4 AD |
| 20 AD | $-CH_3$ | $-CH_3$ | $-H$ | $-OCH_3$ | $-\underset{\underset{O}{\|}}{C}-OCH_3$ | Melting point: 76–77° C. | $[\alpha]_D^{24°C.} = -22.54°$ | 4 AD |
| 91 AD | $-CH_3$ | $-CH_3$ | $-H$ | $-OCH_3$ | $-\underset{\underset{S}{\|}}{C}-SC_2H_5$ | | | 1 |
| 98 AD | $-CH_3$ | $-CH_3$ | $-H$ | $-OCH_3$ | $-\underset{\underset{O}{\|}}{C}-SC_2H_5$ | | | 4 AD |

TABLE 4-continued

Optically active compounds

Formula I in which R denotes $-\overset{CH_3}{\underset{|}{CH}}-COR^5$; $R^3-\!\!\!\!\begin{array}{c}R^1\\\phantom{x}\end{array}\!\!\!\!-N\begin{array}{c}\overset{CH_3}{\underset{|}{C}}{\cdots}H\\COR^5\\COCH_2-S-X\end{array}$ $R^2$

| Example No. | $R^1$ | $R^2$ | $R^3$ | $R^5$ | X | Characteristic physico-chemical data | Specific optical rotation $[\alpha]_D^{t\,°C}$ | Preparation analogous to Example No. |
|---|---|---|---|---|---|---|---|---|
| 2 AD | —CH$_3$ | —CH$_3$ | —H | —OCH$_3$ | $-\underset{\underset{S}{\|}}{C}-OCH_3$ | | | 2 |
| 141 AD | —CH$_3$ | —CH$_3$ | —H | —OCH$_3$ | $-\underset{\underset{O}{\|}}{C}-H$ | | | 4 AD |
| 104 AD | —CH$_3$ | —CH$_3$ | —H | —OCH$_3$ | $-\underset{\underset{O}{\|}}{C}-N(CH_3)_2$ | | | 2 |
| 11 AD | —CH$_3$ | —CH$_3$ | —H | —OCH$_3$ | $-\underset{\underset{S}{\|}}{C}-OCH_2CH_2CH_3$ | | | 1 |

B. Formulation Examples

EXAMPLE A

A dusting agent is obtained by mixing 10 parts by weight of active compound and 90 parts by weight of talc, as the inert substance, and comminuting the mixture in a hammer mill.

EXAMPLE B

A wettable powder which is easily dispersible in water is obtained by mixing 25 parts by weight of active compound, 64 parts by weight of kaolin-containing quartz, as the inert substance, and 10 parts by weight of sodium lignin-sulfonate and 1 part by weight of sodium oleoylmethyl-tauride, as the wetting agent and dispersing agent, and grinding the mixture in a pinned disc mill.

EXAMPLE C

A dispersion concentrate which is easily dispersible in water is obtained by mixing 20 parts by weight of active compound with 6 parts by weight of nonylphenol polyglycol ether (oxyethyleneated with 10 moles of ethylene oxide), 3 parts by weight of isotridecanol polyglycol ether (oxyethyleneated with 8 moles of ethylene oxide) and 71 parts by weight of paraffinic mineral oil (boiling range, for example, about 255° to over 377° C./normal pressure) and grinding the mixture to a fineness of less than 5 microns in a ball mill.

EXAMPLE D

An emulsifiable concentrate is obtained from 15 parts by weight of active compound, 75 parts by weight of cyclohexanone, as the solvent, and 10 parts by weight of oxyethyleneated nonylphenol (oxyethyleneated with 10 moles of ethylene oxide), as the emulsifier.

EXAMPLE E

Granules containing 5% by weight of active compound are obtained from 5 parts by weight of active compound, 0.25 part by weight of epichlorohydrin, 0.25 part by weight of cetyl polyglycol ether, 3.5 parts by weight of polyethylene glycol and 91 parts by weight of kaolin by mixing the active compound with the epichlorohydrin, dissolving the mixture in 6 parts by weight of acetone and then adding the polyethylene glycol and the cetyl polyglycol ether. The resulting solution is sprayed onto kaolin of the desired particle size and is adsorbed by the kaolin. The acetone is then evaporated off in vacuo.

C. Biological Examples

EXAMPLE I

Action of the Claimed Compounds Against *Phytophthora infestans* on *Solanum lycopersicum*

(a) Preventive action

Tomato plants (*Solanum lycopersicum*) of the Rheinlandsruhm variety in the 3-leaf stage are sprayed, until dripping wet, with the compounds of the formula I prepared according to Examples 1 to 152, in an active compound concentration of in each case 500 mg/liter of spray liquor. After the coating sprayed on has dried, the plants are heavily inoculated with a zoosporangia suspension of *Phytophthora infestans* and are placed, dripping wet, for one day in a climatically conditioned chamber at a temperature of 16° C. and a relative atmospheric humidity of almost 100%. They are then placed in a cool greenhouse at a temperature of 15° C. and a relative atmospheric humidity of 90–95%. After an incubation period of 7 days, the plants are examined for infection by Phytophthora. The number and size of the typical Phytophthora leaf spots serve as the evaluation criterion for the activity of the compounds claimed. The degree of infection is expressed in % of infected area of leaf, in comparison with untreated, infected control plants.

The compounds of Examples 1 to 152 cause a reduction in the fungal infection to, on average, less than 20%. A number of compounds of the formula I reduce the fungal attack almost to zero (0–5%) even when substantially lower amounts are applied, as the result obtained with the compounds of the formula I given below in Table Ia shows.

TABLE Ia

| Compounds according to Example No. | % of Phytophthora infection at mg of active compound/liter of spray liquor | | | | |
|---|---|---|---|---|---|
| | 500 | 250 | 125 | 60 | 30 |
| 1 | 0 | 0 | 0 | 0 | 0 |
| 10 | 0 | 0 | 0 | 0 | |
| 13 | 0 | 0 | 0 | 0 | |
| 86 | 0 | 0 | 0 | | |
| 88 | 0 | 0 | 0-3 | | |
| 12 | 0 | 0 | 0 | | |
| 36 | 0 | 0 | 0 | | |
| 48 | 0 | 0 | 0 | | |
| 11 | 0 | 0 | 0 | | |
| 15 | 0 | 0 | 0 | | |
| 16 | 0 | 0 | 0 | | |
| 21 | 0 | 0 | 0-3 | | |
| 45 | 0 | 0 | 0 | | |
| 39 | 0 | 0 | 0 | | |
| 91 | 0 | 0 | 0 | | |
| 96 | 0 | 0 | 0 | | |
| 1 AD | 0 | 0 | 0 | | |
| 19 | 0 | 0 | 0 | | |
| 20 | 0 | 0 | 0 | | |
| 101 | 0 | 0 | 0 | | |
| 102 | 0 | 0 | 0 | | |
| 124 | 0 | 0 | 0 | | |
| 104 | 0 | 0 | 0 | | |
| 8 | 0 | 0 | 0 | | |
| 98 | 0 | 0 | 0 | | |
| untreated infected plants | 100 | | | | |

(b) Curative action

Tomato plants (*Solanum lycopersicum*) of the Rheinlandsruhm variety in the 3-leaf stage are heavily inoculated with a zoosporangia suspension of *Phytophthora infestans* and are incubated for 24 hours in a climatically conditioned chamber at a temperature of 15° C. and a relative atmospheric humidity of almost 100%. After the plants have dried, they are sprayed with compounds of the formula I prepared according to Examples 1 to 152 and formulated as wettable powders, at active compound concentrations in the spray liquors of in each case 500 ppm. The plants are then placed again in a greenhouse at a temperature of about 16° C. and a relative atmospheric humidity of about 90-95%. Five days later, the plants are examined for infection by *Phytophthora infestans*. The number and size of the typical Phytophthora leaf spots serve as a criterion for evaluating the activity of the compounds tested.

The degree of infection is expressed in % of infected area of leaf, in comparison with untreated, infected control plants.

The compounds of Examples 1 to 152 effect a reduction in the Phytophthora infection to, on average, less than 20%. A number of compounds of the formula I reduce the fungal infection virtually to zero even when substantially lower amounts are applied, as the result obtained with the compounds of the formula I given below in Table Ib shows.

TABLE Ib

| Compounds according to Example No. | % of Phytophthora infection at mg of active compound/liter of spray liquor | | | |
|---|---|---|---|---|
| | 500 | 250 | 125 | 60 |
| 1 (formulated as a wettable powder) | 0 | 0 | 0 | 0 |
| 1 (formulated as an emulsion concentrate) | 0 | 0 | 0 | 0 |
| 13 (formulated as a wettable powder) | 0 | 0 | 0 | 0 |
| 5 | 0 | 0 | 0 | |
| 1 AD | 0 | 0 | 0 | 0 |

TABLE Ib-continued

| Compounds according to Example No. | % of Phytophthora infection at mg of active compound/liter of spray liquor | | | |
|---|---|---|---|---|
| | 500 | 250 | 125 | 60 |
| 91 | 0 | 0 | 0 | |
| 20 | 0 | 0 | 0 | |
| 7 | 0 | 0 | 0 | |
| untreated, infected plants | 100 | | | |

(c) Preventive-systemic action

The compounds of the formula I prepared according to Examples 1 to 152 and formulated as wettable powders are applied, in active compound concentrations of in each case 200 ppm (relative to the volume of soil) to the soil surface around potted tomato plants of the Rheinlandsruhm variety which are about 3-4 weeks old. Three days later, the plants are inoculated with a zoosporangia suspension of Phytophthora infestans and are incubated as described under Example Ia. After an incubation period of 6-7 days, the plants are examined for infection by Phytophthora infestans. The number and size of the typical Phytophthora leaf spots formed on the leaves provide the criterion for evaluating the activity of the compounds tested.

The degree of infection is expressed in % of infected area of leaf, in comparison with untreated, infected control plants.

The compounds of Examples 1 to 152 effect a reduction in the fungal infection to, on average, less than 20%. A number of compounds of the formula I virtually completely suppress the fungal infection even when substantially lower amounts are applied, as the result obtained with the compounds of the formula I given below in Table Ic shows.

TABLE Ic

| Compounds according to Example No. | % Phytophthora infection at ppm of active compound in the soil | | | |
|---|---|---|---|---|
| | 200 | 100 | 50 | 25 |
| 1 | 0 | 0 | 0 | 0 |
| 13 | 0 | 0 | 0 | 0 |
| 91 | 0 | 0 | 0 | |
| 20 | 0 | 0 | 0 | |
| 4 AD | 0 | 0 | 0 | |
| untreated, infected plants | 100 | | | |

EXAMPLE II

Action against *Plasmopara viticola* on vines (a) Preventive action

Vines which have been grown from cuttings of the Müller Thurgau variety, which are susceptible to infection by Plasmopara, are sprayed, in the 4-leaf stage, until dripping wet with aqueous suspensions of the compounds of the formula I prepared according to Examples 1 to 152 in an active compound concentration of in each case 500 mg/liter of spray liquor. After the coating sprayed on has dried, the plants are inoculated with a zoosporangia suspension of Plasmopara viticola and are placed, dripping wet, in a climatically conditioned chamber at a temperature of 20° C. and a relative atmospheric humidity of about 100%. After 24 hours, the infected plants are removed from the climatically conditioned chamber and placed in a greenhouse at a temperature of 23° C. and an atmospheric humidity of about 98%. After an incubation period of 7 days, the plants are moistened and placed overnight in the climatically conditioned chamber and the infection is made to break out. The infection is then evaluated. The number and size of the areas of infection on the leaves of the inoculated and treated plants serve as a measure of the activity of the compounds tested. The degree of infection is expressed in % of infected area of leaf, in comparison with untreated, infected control plants.

A substantial suppression of the fungal infection (average degree of infection <20%) is achieved with the compounds of Examples 1 to 152. A number of compounds of the formula I virtually completely suppress the fungal infection even when substantially lower concentrations are applied, as the result obtained with the compounds of the formula I given below in Table II shows.

TABLE II

| Compounds according to Example No. | % of Plasmopara infection at mg of active compound/liter of spray liquor | | | | |
|---|---|---|---|---|---|
| | 500 | 250 | 125 | 60 | 30 |
| 1 | 0 | 0 | 0 | 0 | 0 |
| 10 | 0 | 0 | 0 | 0 | 0 |
| 13 | 0 | 0 | 0 | 0 | 0 |
| 86 | 0 | 0 | 0 | | |
| 89 | 0 | 0 | 0 | | |
| 71 | 0 | 0 | 0 | | |
| 12 | 0 | 0 | 0 | | |
| 22 | 0 | 0 | 0 | | |
| 36 | 0 | 0 | 0 | | |
| 48 | 0 | 0 | 0 | | |
| 11 | 0 | 0 | 0 | | |
| 15 | 0 | 0 | 0 | | |
| 37 | 0 | 0 | 0 | | |
| 16 | 0 | 0 | 0 | | |
| 21 | 0 | 0 | 0 | | |
| 24 | 0 | 0 | 0 | | |
| 45 | 0 | 0 | 0 | | |
| 46 | 0 | 0 | 0 | | |
| 4 AD | 0 | 0 | 0 | | |
| 20 AD | 0 | 0 | 0 | | |
| 19 | 0 | 0 | 0 | | |
| 47 | 0 | 0 | 0 | | |
| 1 AD | 0 | 0 | 0 | | |
| 38 | 0 | 0 | 0 | | |
| 39 | 0 | 0 | 0 | | |
| 91 | 0 | 0 | 0 | | |
| 96 | 0 | 0 | 0 | | |
| 42 | 0 | 0 | 0 | | |
| 51 | 0 | 0 | 0 | | |
| 101 | 0 | 0 | 0 | | |
| 102 | 0 | 0 | 0 | | |
| 104 | 0 | 0 | 0 | | |
| 124 | 0 | 0 | 0 | | |
| 6 | 0 | 0 | 0 | | |
| 142 | 0 | 0 | 0 | | |
| 9 | 0 | 0 | 0 | | |
| 98 | 0 | 0 | 0 | | |
| untreated, infected plants | 100 | | | | |

EXAMPLE III

Action against *Pythium ultimum* on peas (a) Action after application to the soil The fungus is grown in a sand culture and mixed with soil. The soil thus infected is filled, as the growing soil, into pots for growing and is sown with pea seeds. After sowing, the soil surface is watered with the compounds of the formula I prepared according to Examples 1 to 152, as aqueous suspensions in an active compound concentration of in each case 200 ppm (relative to the volume of soil). The pots are then placed in a greenhouse at 20°-22° C. for 2-3 weeks and the soil is kept uniformly slightly moist. In evaluating the Pythium infection, the emergence of the small pea plants and the proportion of healthy and diseased plants are established, in comparison with the corresponding controls, and the degree of action of the compounds tested is calculated therefrom.

A substantial reduction in the Pythium ultimum infection is achieved with the compounds of Examples 1 to 152, the degree of action being on average >80%.

A number of compounds of the formula I effect virtually complete suppression of the fungal infection even at substantially lower concentrations of active compound, as the results obtained with the compounds of the formula I given below in Table III show.

TABLE III

Fungicidal action against Pythium ultimum after treatment of inoculated growing soil with the given compounds of the formula I, as the active compound, in the concentrations indicated and after subsequent sowing of healthy pea seeds.

1st day: Inoculation and treatment of the soil with the active compound, sowing;
14th day: Evaluation

| Compounds according to Example No. | Degree of fungicidal action in % at ppm of active compound in the soil | | | |
|---|---|---|---|---|
| | 200 | 100 | 50 | 25 |
| 1 | 100 | 100 | 100 | 100 |
| 86 | 100 | 100 | | |
| 12 | 100 | 100 | 100 | |
| 1 AD | 100 | 100 | 100 | |
| 4 AD | 100 | 100 | 100 | |
| 20 | 100 | 100 | 100 | |
| 36 | 100 | 100 | | |
| 48 | 100 | 100 | 100 | |
| 11 | 100 | 100 | 100 | |
| 15 | 100 | 100 | 100 | |
| 38 | 100 | 100 | | |
| 39 | 100 | 100 | | |
| 91 | 100 | 100 | 100 | |
| 96 | 100 | 100 | | |
| 10 AD | 100 | 100 | 100 | |
| 10 | 100 | 100 | 100 | |
| 98 | 100 | 100 | 100 | |
| 102 | 100 | 100 | | |
| 104 | 100 | 100 | 100 | |
| 115 | 100 | 100 | | |
| 124 | 100 | 100 | 100 | |
| Comparison agent A* | 65 | 40 | 0 | |
| Untreated, inoculated soil | 0 (= 100% emergence damage) | | | |
| Untreated, non-inoculated soil | 100% emergence | | | |

*Comparison agent A: Methyl 2-[N-(methylthioacetyl)-N-(2,6-dimethylphenyl)-amino]-propionate (compare German Offenlegungsschrift 2,515,091).

EXAMPLE IV

Preventive action of the compounds of the formula I against *Phytophthora capsici* (soil application)

*Phytophthora capsici* is grown in sand cultures and mixed with experimental soil. The soil thus infected is filled into pots for growing and sown with paprika (*Capsicum annuum*). After sowing, the surface of the soil is watered with the compounds claimed, as aqueous suspensions, or the aqueous suspensions are incorporated into the covering layer of soil. Active compound concentrations of 200 to 50 ppm (relative to the volume of the soil) are applied. The pots are then placed in a greenhouse at 22°-24° C. for about 3 weeks and the growing soil is kept uniformly moist. In the evaluation for *Phytophthora capsici* infection, the emergence of the paprika plants and the proportion of healthy and diseased plants are established, in comparison with the corresponding controls, and the degree of action is calculated accordingly.

The compounds of the formula I in general effect complete control of the *Phytophthora capsici* infection when applied in an amount of 200 ppm. A number of compounds of the formula I also lead to a reduction in the fungal infection to zero even when considerably smaller amounts are applied, as shown below by the test results summarized in Table IV.

TABLE IV

Action against Phytophthora capsici after treatment of inoculated soil with fungicidal compounds of the formula I and sowing of healthy paprika seeds.

1st day: inoculation of the soil and treatment with the fungicidal compound, sowing
About the 21st day: evaluation

| Compound according to Example No. | Degree of action in % at ppm of active compound in the soil 200 ppm | 100 ppm | 50 ppm |
|---|---|---|---|
| 12 | 100 | 100 | 100 |
| 36 | 100 | 100 | 100 |
| 11 | 100 | 100 | 100 |
| 15 | 100 | 100 | 95 |
| 91 | 100 | 100 | 100 |
| 96 | 100 | 100 | 100 |
| 1 | 100 | 100 | 100 |
| 10 | 100 | 100 | 100 |
| 1 AD | 100 | 100 | 100 |
| 20 | 100 | 100 | 100 |
| 20 AD | 100 | 100 | 100 |
| 98 | 100 | 100 | 100 |
| 104 | 100 | 100 | 100 |
| 124 | 100 | 100 | 100 |
| Control: | | | |
| Untreated, inoculated soil | 0 (= 100% emergence damage) | | |
| Untreated, non-inoculated soil | 100% emergence | | |

We claim:

1. Compound of the formula 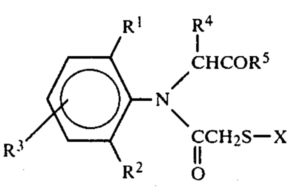 in which X is or hydrogen; $R^1$ is $(C_1-C_4)$-alkyl, halogen, $(C_1-C_3)$-alkylthio, $(C_1-C_4)$-alkoxy or $(C_3-C_4)$-alkenyl; $R^2$ is hydrogen, $(C_1-C_4)$-alkyl or halogen; $R^3$ and $R^4$ are hydrogen or methyl; $R^5$ is hydroxyl, $(C_1-C_4)$-alkoxy, $(C_1-C_3)$-alkylthio, $(C_1-C_2)$-alkoxy-$(C_1-C_2)$-alkoxy, amino, $(C_1-C_2)$-alkylamino or di-$(C_1-C_2)$-alkylamino; Y is oxygen or sulfur; $R^7$ is $(C_1-C_6)$-alkyl, $(C_1-C_6)$-alkyl substituted by methoxy, ethoxy or halogen, or $(C_3-C_6)$-cycloalkyl, $(C_3-C_4)$-alkenyl or $(C_3-C_4)$-alkynyl; $R^8$ is hydrogen or $(C_1-C_4)$-alkyl and when Y is S is hydrogen, $R^9$ is $(C_1-C_4)$-alkyl, $(C_1-C_4)$-alkyl substituted by halogen or $(C_1-C_2)$-alkoxy, or $(C_3-C_4)$-alkenyl, furfuryl or tetrahydrofurfuryl; $R^{10}$ is -CN, $(C_1-C_4)$-alkyl, $(C_1-C_4)$-alkyl, substituted by halogen or $(C_1-C_2)$-alkoxy, or allyl or furfuryl; and $R^{11}$ is hydrogen, $(C_1-C_4)$-alkyl, $(C_1-C_4)$-alkyl substituted by one or three halogen atoms, $(C_1-C_2)$-alkoxy or $(C_1-C_2)$-alkylthio, or $(C_2-C_4)$-alkenyl.

2. The compound defined in claim 1, which is methyl-2-[N-2,6-dimethylphenyl)-N-(ethoxythiocarbonylthioacetyl)-amino)-propionate.

3. Fungicidal composition containing, as an active component, a fungicidally effective amount of a compound defined in claim 1 and a suitable inert diluent.

4. A method for combating fungus which comprises applying to the site of a fungus infection or potential fungus infection a fungicidally effective concentration of a compound defined in claim 1.

5. Compound of the formula 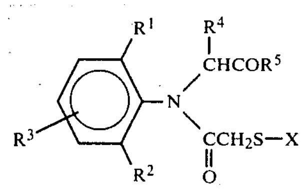 in which X is 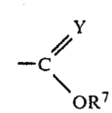 $R^1$ is $(C_1-C_4)$-alkyl, halogen, $(C_1-C_3)$-alkylthio, $(C_1-C_4)$-alkoxy or $(C_3-C_4)$-alkenyl; $R^2$ is hydrogen, $(C_1-C_4)$-alkyl or halogen; $R^3$ and $R^4$ are hydrogen or methyl; $R^5$ is hydroxyl, $(C_1-C_4)$-alkoxy, $(C_1-C_3)$-alkylthio, $(C_1-C_2)$-alkoxy-ethoxy, amino, $(C_1-C_2)$-alkylamino or di-$(C_1-C_2)$-alkylamino; Y is oxygen or sulfur; $R^7$ is $(C_1-C_6)$-alkyl, $(C_1-C_6)$-alkyl substituted by methoxy, ethoxy or halogen or $(C_3-C_6)$-cycloalkyl, $(C_3-C_4)$-alkenyl or $(C_3-C_4)$-alkynyl.

6. Compound of the formula 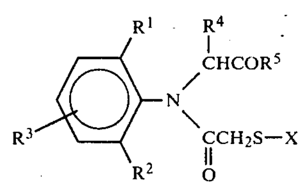 in which X is 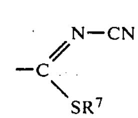 $R^1$ is $(C_1-C_4)$-alkyl, halogen, $(C_1-C_3)$-alkylthio, $(C_1-C_4)$-alkoxy or $(C_3-C_4)$-alkenyl; $R^2$ is hydrogen, $(C_1-C_4)$-alkyl or halogen; $R^3$ and $R^4$ are hydrogen or methyl; $R^5$ is hydroxyl, $(C_1-C_4)$-alkoxy, $(C_1-C_3)$-alkylthio, $(C_1-C_2)$-alkoxy-$(C_1-C_2)$-alkoxy, amino, $(C_1-C_2)$-alkylamino or di-$(C_1-C_2)$-alkylamino; Y is oxygen or sulfur; $R^7$ is $(C_1-C_6)$-alkyl, $(C_1-C_6)$-alkyl substituted by methoxy, ethoxy or halogen, or $(C_3-C_6)$-cycloalkyl, $(C_3-C_4)$-alkenyl or $(C_3-C_4)$-alkynyl.

* * * * *